United States Patent
Funahashi

(10) Patent No.: US 7,737,628 B2
(45) Date of Patent: Jun. 15, 2010

(54) AROMATIC AMINE DERIVATIVE AND ORGANIC ELECTROLUMINESCENCE DEVICE USING THE SAME

(75) Inventor: Masakazu Funahashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 588 days.

(21) Appl. No.: 11/336,857

(22) Filed: Jan. 23, 2006

(65) Prior Publication Data
US 2006/0194074 A1    Aug. 31, 2006

(30) Foreign Application Priority Data
Feb. 7, 2005   (JP) .............................. 2005-030580

(51) Int. Cl.
C09K 11/06 (2006.01)
H01L 51/54 (2006.01)
H05B 33/14 (2006.01)
C07C 211/43 (2006.01)

(52) U.S. Cl. .................. 313/504; 313/506; 257/40; 257/E51.051; 428/690; 428/917; 564/308

(58) Field of Classification Search ............... 428/690, 428/917; 564/426–434
See application file for complete search history.

(56) References Cited

U.S. PATENT DOCUMENTS

| | | | |
|---|---|---|---|
| 3,951,693 | A | 4/1976 | Fisher et al. |
| 5,811,834 | A | 9/1998 | Tamano et al. |
| 6,743,948 | B1 | 6/2004 | Hosokawa et al. |
| 7,425,653 | B2 * | 9/2008 | Funahashi .................. 564/434 |
| 2005/0038296 | A1 | 2/2005 | Hosokawa et al. |
| 2006/0052641 | A1 | 3/2006 | Funahashi |
| 2006/0202190 | A1 | 9/2006 | Funahashi |

FOREIGN PATENT DOCUMENTS

| | | |
|---|---|---|
| EP | 0 106 112 A1 | 4/1984 |
| EP | 0 786 926 A2 | 7/1997 |
| EP | 1 561 794 A1 | 8/2005 |
| JP | 9-268283 | 10/1997 |
| JP | 2001-052868 | 2/2001 |
| JP | 2001-131541 | 5/2001 |
| WO | WO 00/039247 A1 | 7/2000 |
| WO | WO 2004/044088 A1 | 5/2004 |
| WO | WO 2004092111 * | 10/2004 |

OTHER PUBLICATIONS

U.S. Appl. No. 11/575,441, filed Mar. 16, 2007, Funahashi.
U.S. Appl. No. 11/550,519, filed Oct. 18, 2006, Funahashi.
U.S. Appl. No. 11/596,299, filed Nov. 13, 2006, Funahashi.
U.S. Appl. No. 11/336,855, filed Jan. 23, 2006, Funahashi, et al.
U.S. Appl. No. 11/344,604, filed Feb. 1, 2006, Hosokawa, et al.
U.S. Appl. No. 11/282,697, filed Nov. 21, 2005, Funahashi.

* cited by examiner

*Primary Examiner*—D. Lawrence Tarazano
*Assistant Examiner*—Brett A Crouse
(74) *Attorney, Agent, or Firm*—Oblon, Spivak, McClelland, Maier & Neustadt, L.L.P.

(57) ABSTRACT

An aromatic amine derivative with a specified structure whose benzene ring is bonded with a cycloalkyl group. An organic electroluminescence device which comprises at least one organic thin film layer comprising a light emitting layer sandwiched between a pair of electrode consisting of an anode and a cathode, wherein at least one of the organic thin film layer comprises the aromatic amine derivative singly or in combination. The organic EL device employing the aromatic amine derivative reveals practically sufficient luminance even under low applied voltage, exhibits an enhanced efficiency of light emission, and is resistant to degrade even after a long time usage demonstrating a prolonged lifetime.

15 Claims, 4 Drawing Sheets

AROMATIC AMINE DERIVATIVE AND ORGANIC ELECTROLUMINESCENCE DEVICE USING THE SAME

TECHNICAL FIELD

The present invention relates to an aromatic amine derivative and an organic electroluminescence device using the derivative and, more particularly, to an organic electroluminescence device having long lifetime, a high efficiency of light emission and emitting blue light of a high purity and an aromatic amine derivative realizing the organic electroluminescence device.

BACKGROUND ART

Organic EL devices which utilize organic substances are expected to be useful for application as an inexpensive full color display device of the solid light emission type having a great size and various developments on the organic EL devices are being conducted. In general, an organic EL device has a construction comprising a light emitting layer and a pair of electrodes sandwiching the light emitting layer. The light emission of the organic EL device is a phenomenon in which, when an electric field is applied between the two electrodes, electrons are injected from the cathode side and holes are injected from the anode side, the electrons are recombined with the holes in the light emitting layer to form an excited state, and energy generated when the excited state returns to the ground state is emitted as light.

As compared with an inorganic light emitting diode, conventional organic EL devices requires high driving voltage and only exhibited low luminance or low efficiency of light emission. Moreover, characteristic degradation of the conventional organic EL devices was also extravagant and as a result, they were not practically used. Although recent organic EL devices are improved step by steps, it has been still demanded to develop organic EL devices operable at low driving voltage, with excellent luminance and favorable efficiency of light emission.

For example, there is disclosed such a technique using a single monoanthracene compound as an organic light-emitting material (refer to Patent Literature 1 below). However, in this technique, a luminance obtained by using the material is as low as 1650 cd/m$^2$, for example, at a current density of 165 mA/cm$^2$, and an efficiency of light emission thereof is very low, i.e., only 1 cd/A, which is practically unusable. Also, there is disclosed a technique using a single bisanthracene compound as an organic light emitting material (refer to Patent Literature 2 below). However, in this technique, a current efficiency of light emission obtained by using the material is also as low as about 1 to 3 cd/A. Therefore, further improvement of the technique has bee demanded for rendering it practically usable. Further, there is disclosed a technique using a mono- or bis-anthracene compound together with a distearyl compound in an organic light emitting medium layer (refer to Patent Literature 3 below). However, the device described therein fails to show a sufficiently long half lifetime and, therefore, further improvement has been demanded.

Furthermore, a technique of employing mono or bis-anthracene compound and a di styryl compound as an organic light emitting medium layer is disclosed (refer to Patent Literature 4 below). However in those technologies, a conjugated structure of the styryl compound lengthened wave length of a light emission spectrum and deteriorated the purity of color.

Still further, Patent Literature 5 below discloses a blue luminescence device with the use of diamino chrysene derivatives. However, despite the superiority in efficiency of light emission, because the devices are not sufficient in its lifetime, further improvement was required.

Patent Literature 1: Japanese Unexamined Patent Application Laid-Open No. Hei 11-3782

Patent Literature 2: Japanese Unexamined Patent Application Laid-Open No. Hei 8-12600

Patent Literature 3: International Application Published under PCT No. WO 00/06402

Patent Literature 4: Japanese Unexamined Patent Application Laid-Open No. 2001-284050

Patent Literature 5: International Application Published under PCT No. WO 04/04088

DISCLOSURE OF THE INVENTION

The present invention has been made to overcome the above problems and has an object of providing an organic EL device which emits blue light with high purity and of long lifetime, and an object of providing an aromatic amine derivative realizing the EL device.

As a result of extensive researches for developing aromatic amine derivatives having the above suitable properties and organic EL devices using the aromatic amine derivatives, the inventors have found that the object of the present invention can be achieved by employing an aromatic amine derivative represented by any one of following general formula (1) or general formula (2) whose diphenylamino group having a benzene ring is bonded with a cycloalkyl group. Such being the case, the present invention has been accomplished on the basis of the foregoing findings and information.

Thus, the present invention provides an aromatic amine derivative represented by any one of following general formula (1) or general formula (2):

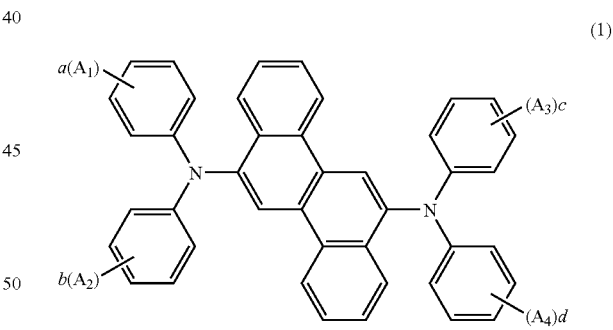

(1)

In the general formula (1), $A_1$ to $A_4$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms or a halogen atom;

a, b, c and d each independently represents an integer of 0 to 5; when a, b, c and d each are 2 or greater, $A_1$ to $A_4$ may be the same with or different from each other, and may bond each other to form a saturated or unsaturated ring; and further, a couple of $A_1$ and $A_2$, and a couple of $A_3$ and $A_4$ may bond each other to form a saturated or unsaturated ring.

however, at least one of a, b, c and d is an integer of 1 or greater, and in this occasion, at least one of $A_1$ to $A_4$ is a substituted or unsubstituted cycloalkyl group having 3 to 50 ring carbon atoms.

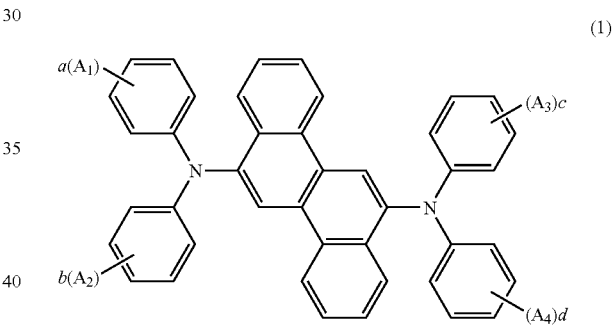

(2)

In the general formula (2), $A_5$ to $A_8$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms or a halogen atom;

e, f, g and h each independently represents an integer of 0 to 5; when e, f, g and h each are 2 or more, $A_5$ to $A_8$ may be the same with or different from each other, and may bond each other to form a saturated or unsaturated ring; and further, a couple of $A_5$ and $A_6$, and a couple of $A_7$ and $A_8$ may bond each other to form a saturated or unsaturated ring;

$X_1$ and $X_2$ each independently represents a substituted or unsubstituted arylene group having 5 to 50 ring carbon atoms;

however, at least one of e, f, g and h is an integer of 1 or greater, and in this occasion, at least one of $A_5$ to $A_8$ is a substituted or unsubstituted cycloalkyl group having 3 to 50 ring carbon atoms.

Further, the present invention provides an organic EL device which comprises at least one organic thin film layer comprising a light emitting layer sandwiched between a pair of electrode consisting of an anode and a cathode, wherein at least one of the organic thin film layer comprises the aromatic amine derivative singly or as its mixture component.

The organic EL device employing the aromatic amine derivative of the present invention reveals practically sufficient luminance even under low applied voltage, exhibits an enhanced efficiency of light emission, and is resistant to degrade even after a long time usage demonstrating a prolonged lifetime.

PREFERRED EMBODIMENT TO CARRY OUT THE INVENTION

Figure 1:
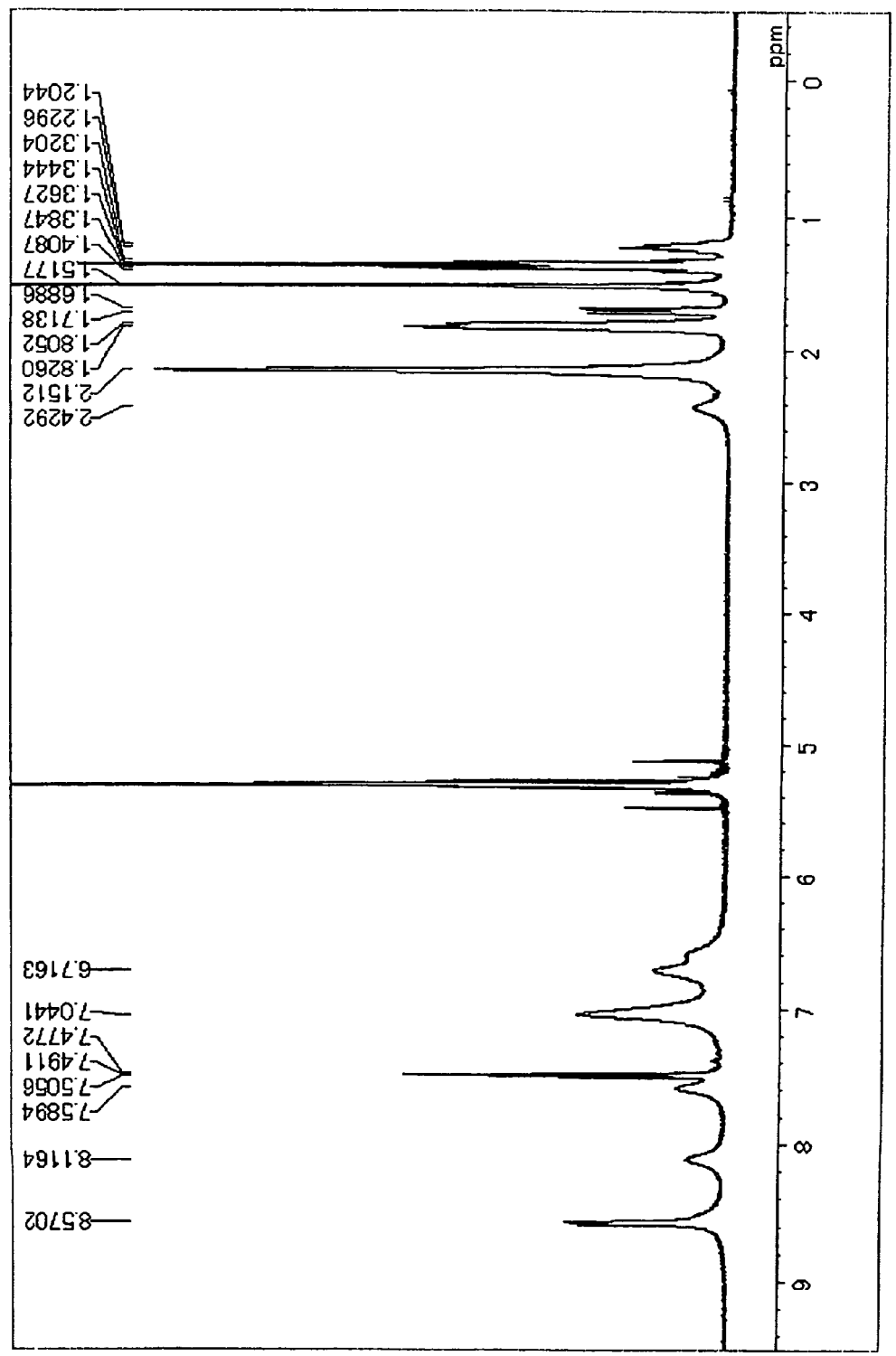
FIG. 1 is a chart showing $^1$H-Nuclear Magnetic Resonance (NMR) spectrum of the aromatic amine derivative of the present invention obtained in Synthesis Example 1.

The present invention provides an aromatic amine derivative represented by any one of following general formula (1) or general formula (2).

The aromatic amine derivative represented by the general formula (1) will be explained below.

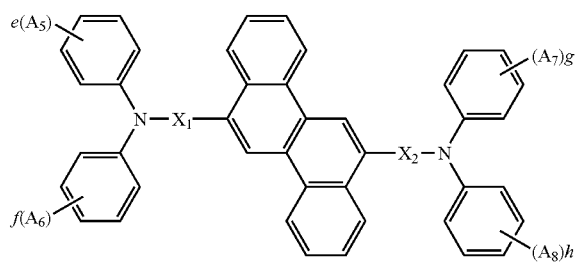

(1)

In the general formula (1), $A_1$ to $A_4$ each independently represents a hydrogen atom, a substituted or unsubstituted alkyl group having 1 to 50 (preferably 1 to 20) carbon atoms, a substituted or unsubstituted aryl group having 5 to 50 (preferably 5 to 20) ring carbon atoms, a substituted or unsubstituted aralkyl group having 6 to 50 (preferably 6 to 20) ring carbon atoms, a substituted or unsubstituted cycloalkyl group having 3 to 50 (preferably 5 to 12) ring carbon atoms, a substituted or unsubstituted alkoxyl group having 1 to 50 (preferably 1 to 6) carbon atoms, a substituted or unsubstituted aryloxy group having 5 to 50 (preferably 5 to 18) ring carbon atoms, a substituted or unsubstituted arylamino group having 5 to 50 (preferably 5 to 18) carbon atoms, a substituted or unsubstituted alkylamino group having 1 to 20 (preferably 1 to 6) carbon atoms, a substituted or unsubstituted heterocyclic group having 5 to 50 (preferably 5 to 20) ring carbon atoms or a halogen atom.

Examples of the substituted or unsubstituted alkyl group represented by $A_1$ to $A_4$ include methyl group, ethyl group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenylbenzyl group, α,α-ditrifluoromethylbenzyl group, triphenylmethyl group, α-benzyloxybenzyl group, etc.

Examples of the substituted or unsubstituted aryl group represented by $A_1$ to $A_4$ include phenyl group, 2-methylphenyl group, 3-methylphenyl group, 4-methylphenyl group, 4-ethylphenyl group, biphenyl group, 4-methyl biphenyl group, 4-ethyl biphenyl group, 4-cyclohexylbiphenyl group, terphenyl group, 3,5-dichlorophenyl group, naphthyl group, 5-methylnaphthyl group, anthryl group, pyrenyl group, etc.

Examples of the substituted or unsubstituted aralkyl group represented by $A_1$ to $A_4$ include benzyl group, α,α-methylphenylbenzyl group, triphenylmethyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethy group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, α-phenoxybenzyl group, α-benzyloxy benzyl group, α,α-ditrifluoromethylbenzyl group, 1-pyrrolylmethyl group, 2-(1-pyrrolyl)ethyl, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group, etc.

Examples of the cycloalkyl group represented by $A_1$ to $A_4$ include cyclopropyl group, cyclobutyl group, cyclopentyl group, cyclohexyl group, cyclo octyl group, cyclo nonyl group, bicycloheptyl group, bicyclo octyl group, tricycloheptyl group, adamanthyl group, etc. Among those, cyclopentyl group, cyclohexyl group, cycloheptyl group, bicycloheptyl group, bicyclo octyl group, and adamanthyl group are prferable.

Examples of the alkoxy group represented by $A_1$ to $A_4$ include methoxy group, ethoxy group, propoxy group, isopropoxy group, butoxy group, isobutoxy group, sec-butoxy group, tert-butoxy group, various kinds of pentyloxy groups, various kinds of hexyloxy groups, etc.

Examples of the aryloxy group represented by $A_1$ to $A_4$ include phenoxy group, tolyloxy group, naphthyloxy group, etc.

Examples of the arylamino group represented by $A_1$ to $A_4$ include diphenylamino group, ditolylamino group, dinaphthylamino group, naphthylphenylamino group, etc.

Examples of the alkylamino group represented by $A_1$ to $A_4$ include dimethylamino group, diethylamino group, dihexylamino group, etc.

Examples of the heterocyclic group represented by $A_1$ to $A_4$ include moieties of imidazole, benzimidazole, pyrrole, furan, thiophene, benzothiophene, oxadiazoline, indoline, carbazole, pyridine, a quinoline, isoquinoline, benzoquinone, pyrazoline, imidazolidine, piperidine, etc.

Examples of the halogen atom represented by $A_1$ to $A_4$ include fluorine atom, chlorine atom, bromine atom, etc.

In the general formula (1), a, b, c and d each independently represents an integer of 0 to 5, preferably an integer of 0 to 3, and more preferably an integer of 0 to 2.

When a, b, c and d each are 2 or more, $A_1$ to $A_4$ may be the same with or different from each other, and may bond each other to form a saturated or unsaturated ring; and further, a couple of $A_1$ and $A_2$, and a couple of $A_3$ and $A_4$ may each other to form a saturated or unsaturated ring.

Examples of the ring include a cycloalkane having 4 to 12 carbon atoms such as cyclobutane, cyclopentane, cyclohexane, adamantane, norbornane, etc.; a cycloalkene having 4 to 12 carbon atoms such as cyclobutene, cyclopentene, cyclohexene, cycloheptene, cyclo octene, etc.; a cycloalkadiene having 6 to 12 carbon atoms such as cyclohexadiene, cycloheptadiene, cyclo octadiene, etc.; an aromatic ring having 6 to 50 carbon atoms such as benzene, naphthalene, phenanthrene, anthracene, pyrene, chrysene, acenaphthylene, etc.; and a heterocyclic group having 5 to 50 carbon atoms such as imidazole, pyrrole, furan, thiophene, pyridine, etc.

Examples of the substituent for $A_1$ to $A_4$ include a substituted or unsubstituted aryl group having 5 to 50 ring carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring carbon atoms, a substituted or unsubstituted arylthio group having 5 to 50 ring carbon atoms, a substituted or unsubstituted alkoxycarbonyl group having 1 to 50 carbon atoms, an amino group, a halogen atom, a cyano group, a nitro group, a hydroxyl group, a carboxyl group, etc.

In the general formula (1), at least one of a, b, c and d is an integer of 1 or greater, and in this occasion, at least one of $A_1$ to $A_4$ is a substituted or unsubstituted cycloalkyl group having 3 to 50 ring carbon atoms, which is preferably a cyclopentyl group, a cyclohexyl group, a cycloheptyl group, a bicycloheptyl group, a bicyclo octyl group or an adamanthyl group.

Next, the aromatic amine derivative represented by the general formula (2) will be explained below.

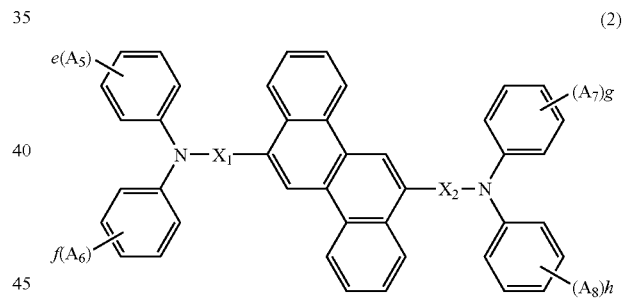

(2)

In the general formula (2), $A_5$ to $A_8$ are the same as explained about the foregoing $A_1$ to $A_4$ in the general formula (1) including the specific examples or the preferable examples.

In the general formula (2), e, f, g and h each independently represents an integer of 0 to 5, preferably an integer of 0 to 3, and more preferably an integer of 0 to 2.

When e, f, g and h each are 2 or more, $A_5$ to $A_8$ may be the same with or different from each other, and may bond each other to form a saturated or unsaturated ring; and further, a couple of $A_5$ and $A_6$, and a couple of $A_7$ and $A_8$ may each other to form a saturated or unsaturated ring; and examples of the ring are the same as explained about $A_1$ to $A_4$ in the general formula (1).

In the general formula (2), $X_1$ and $X_2$ each independently represents a substituted or unsubstituted arylene group having 5 to 50 ring carbon atoms.

Examples of the arylene group represented by $X_1$ and $X_2$ include phenylene group, naphthylene group, biphenylene group, anthranylene group, perylenylene group, pyrenylene group, etc.; phenylene group, naphthylene group, and biphenylene group being preferable.

In the general formula (2), at least one of e, f, g and h is an integer of 1 or greater, and in this occasion, at least one of $A_5$ to $A_8$ is a substituted or unsubstituted cycloalkyl group having 3 to 50 ring carbon atoms, which is preferably a cyclopentyl group, a cyclohexyl group, a cycloheptyl group, a bicycloheptyl group, a bicyclo octyl group or an adamanthyl group.

Specific examples of the aromatic amine derivatives represented by the general formula (1) or (2) will be shown below, though not particularly limited thereto. Meanwhile, in the following compounds, Me represents a methyl group.

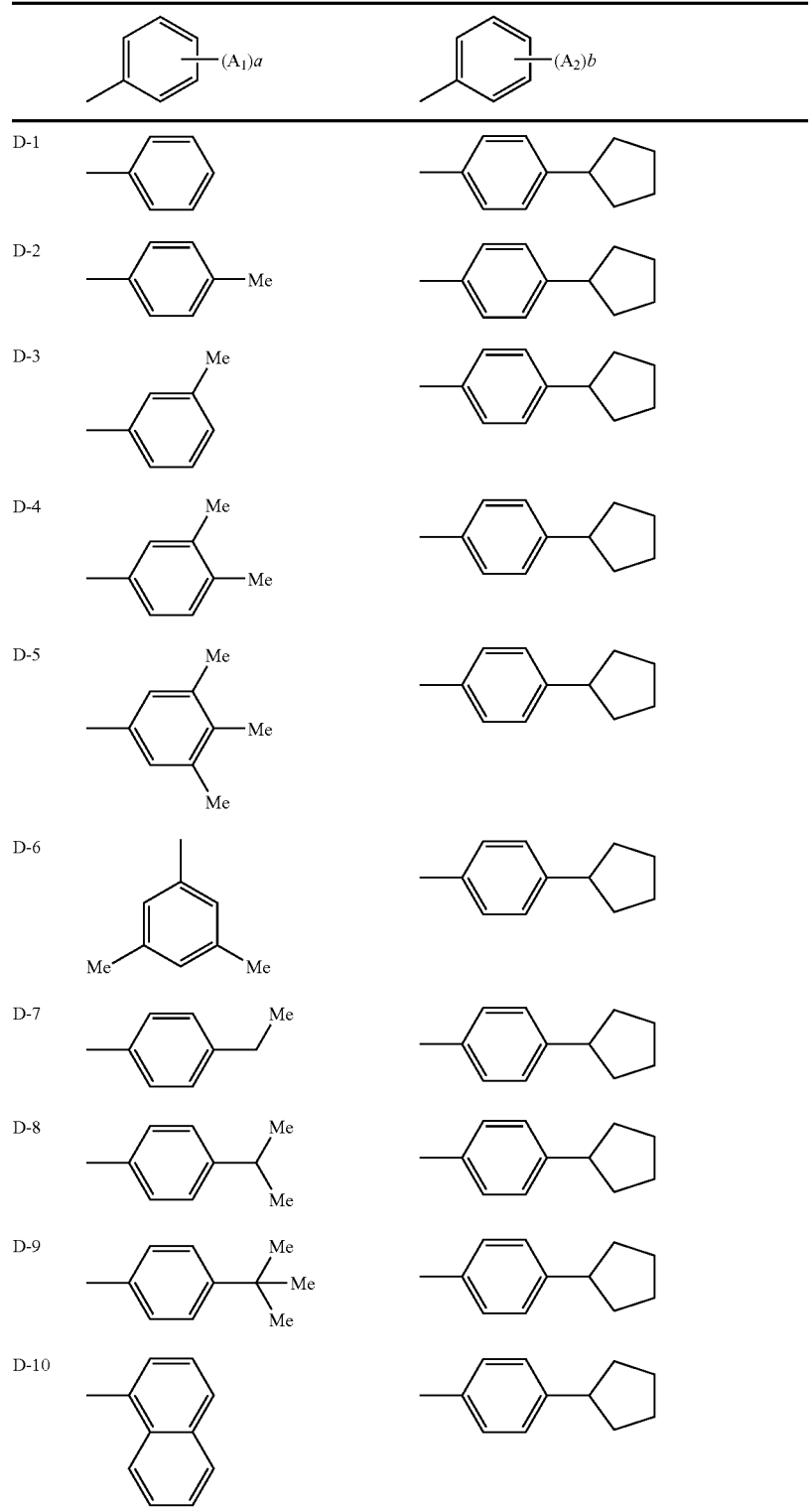

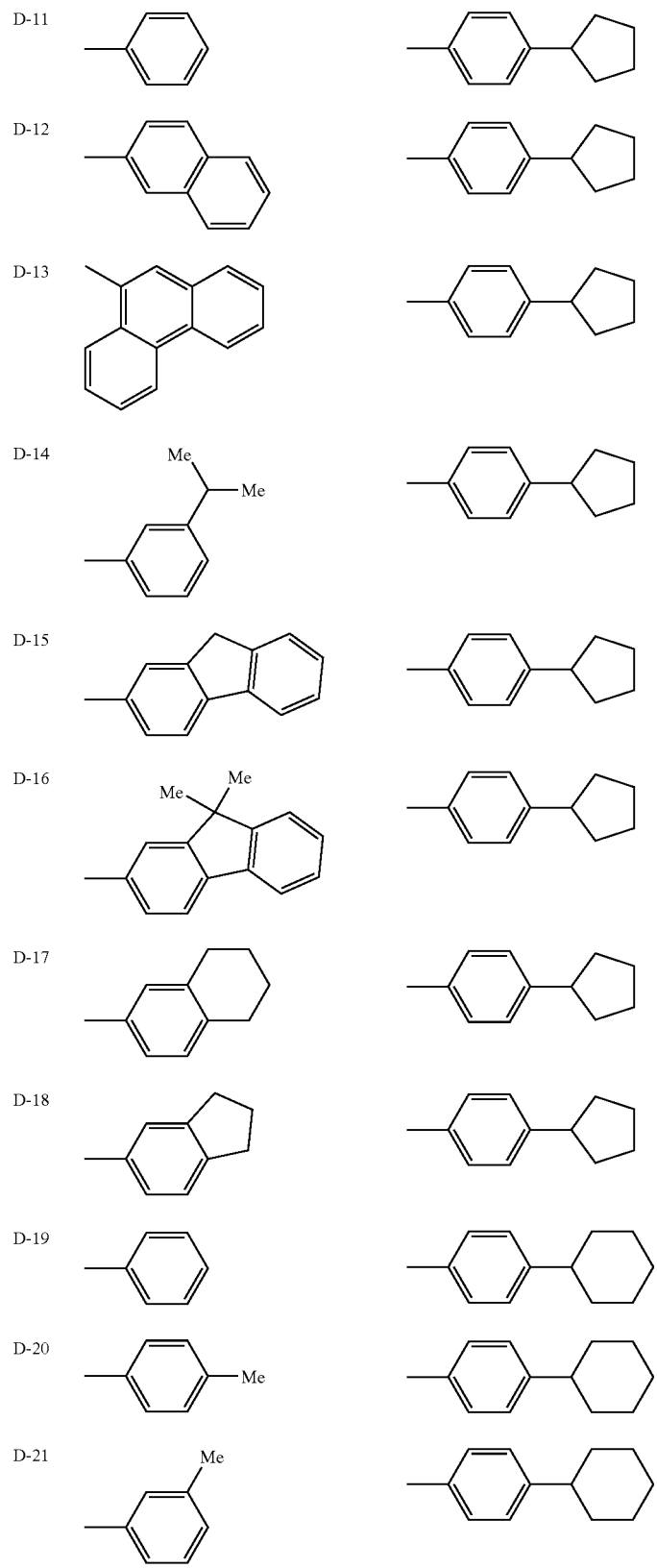

-continued
| | | |
|---|---|---|
| D-22 | 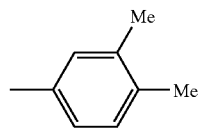 | 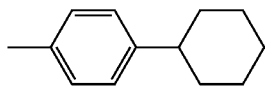 |
| D-23 | 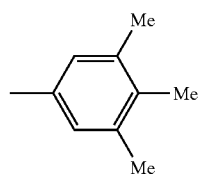 | 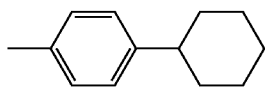 |
| D-24 | 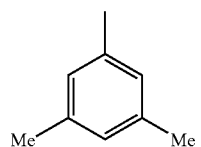 | 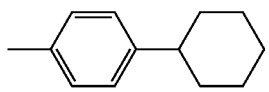 |
| D-25 | 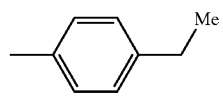 | 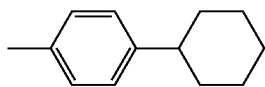 |
| D-26 | 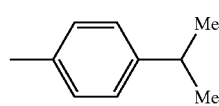 | 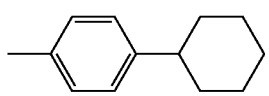 |
| D-27 | 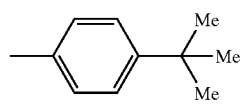 | 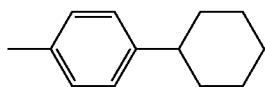 |
| D-28 | 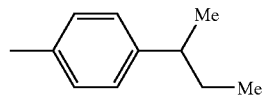 | 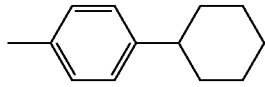 |
| D-29 | 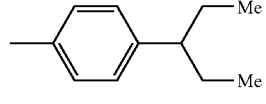 | 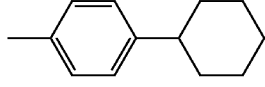 |
| D-30 | 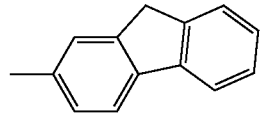 | 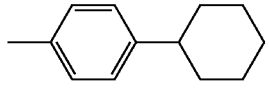 |
| D-31 | 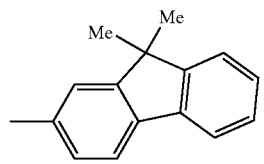 | 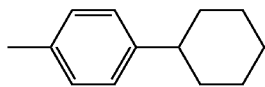 |
| D-32 | 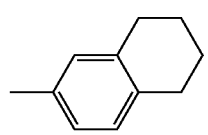 | 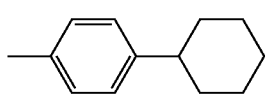 |
| D-33 | 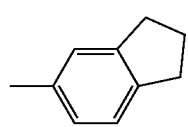 | 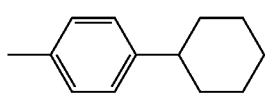 |

-continued
| | | |
|---|---|---|
| D-34 | 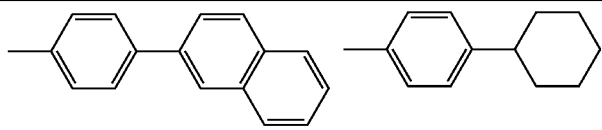 | |
| D-35 |  | |
| D-36 | 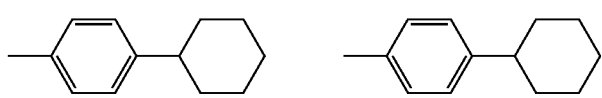 | |
| D-37 |  | |
| D-38 |  | |
| D-39 |  | |
| D-40 |  | |
| D-41 | 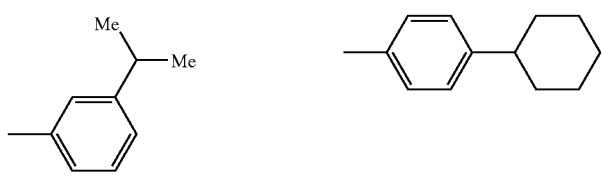 | |
| D-42 | 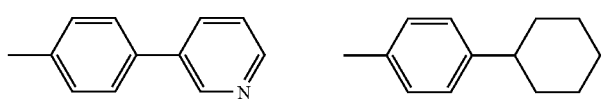 | |
| D-43 | 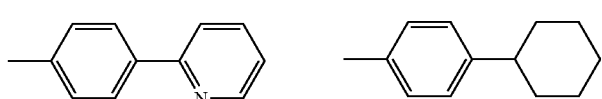 | |
| D-44 | 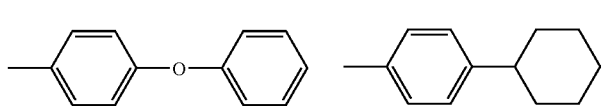 | |
| D-45 |  | |
| D-46 |  | |

-continued
D-47 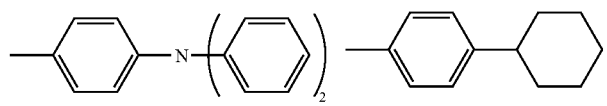
D-48 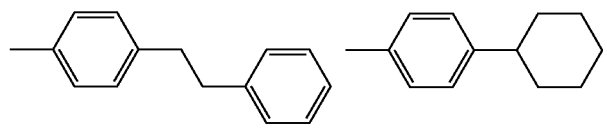
D-49 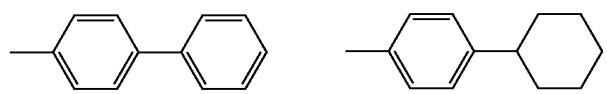
D-50 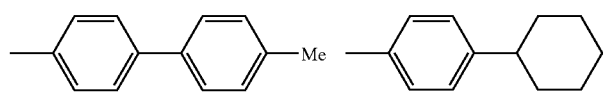
D-51 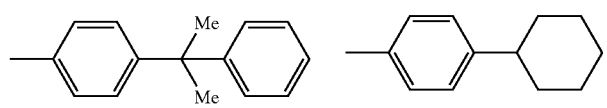
D-52 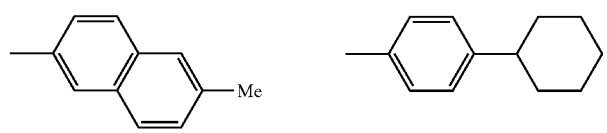
D-53 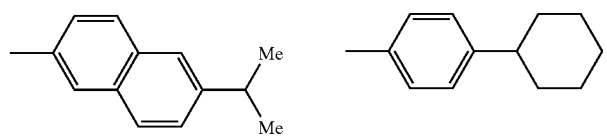
D-54 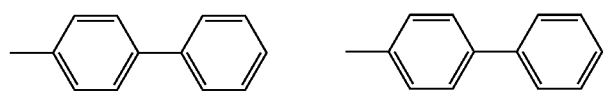
D-55 
D-56 
D-57 
D-58 

-continued
| | | |
|---|---|---|
| D-59 | 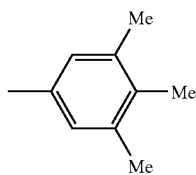 | 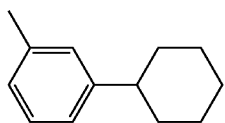 |
| D-60 | 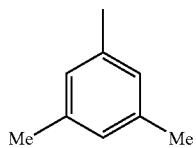 | 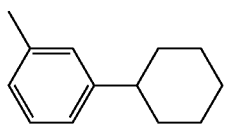 |
| D-61 | 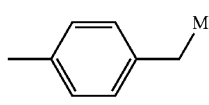 | 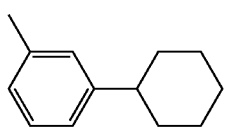 |
| D-62 | 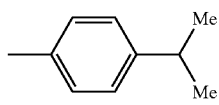 | 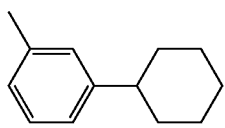 |
| D-63 | 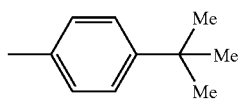 | 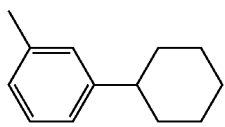 |
| D-64 | 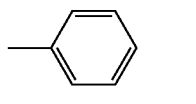 | 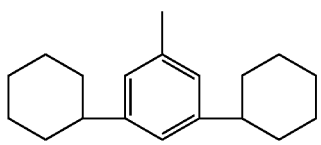 |
| D-65 | 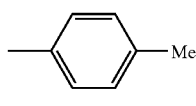 | 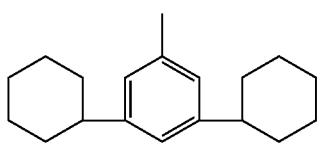 |
| D-66 | 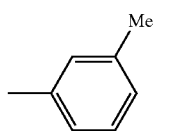 | 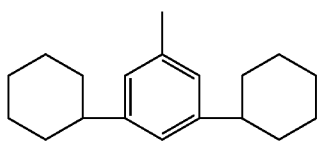 |
| D-67 | 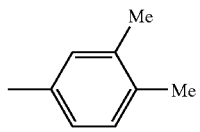 | 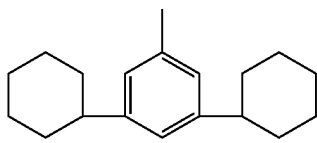 |
| D-68 | 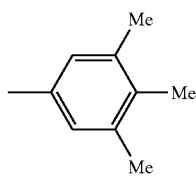 | 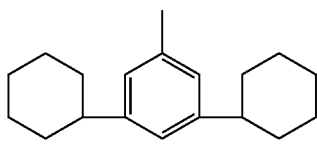 |

-continued
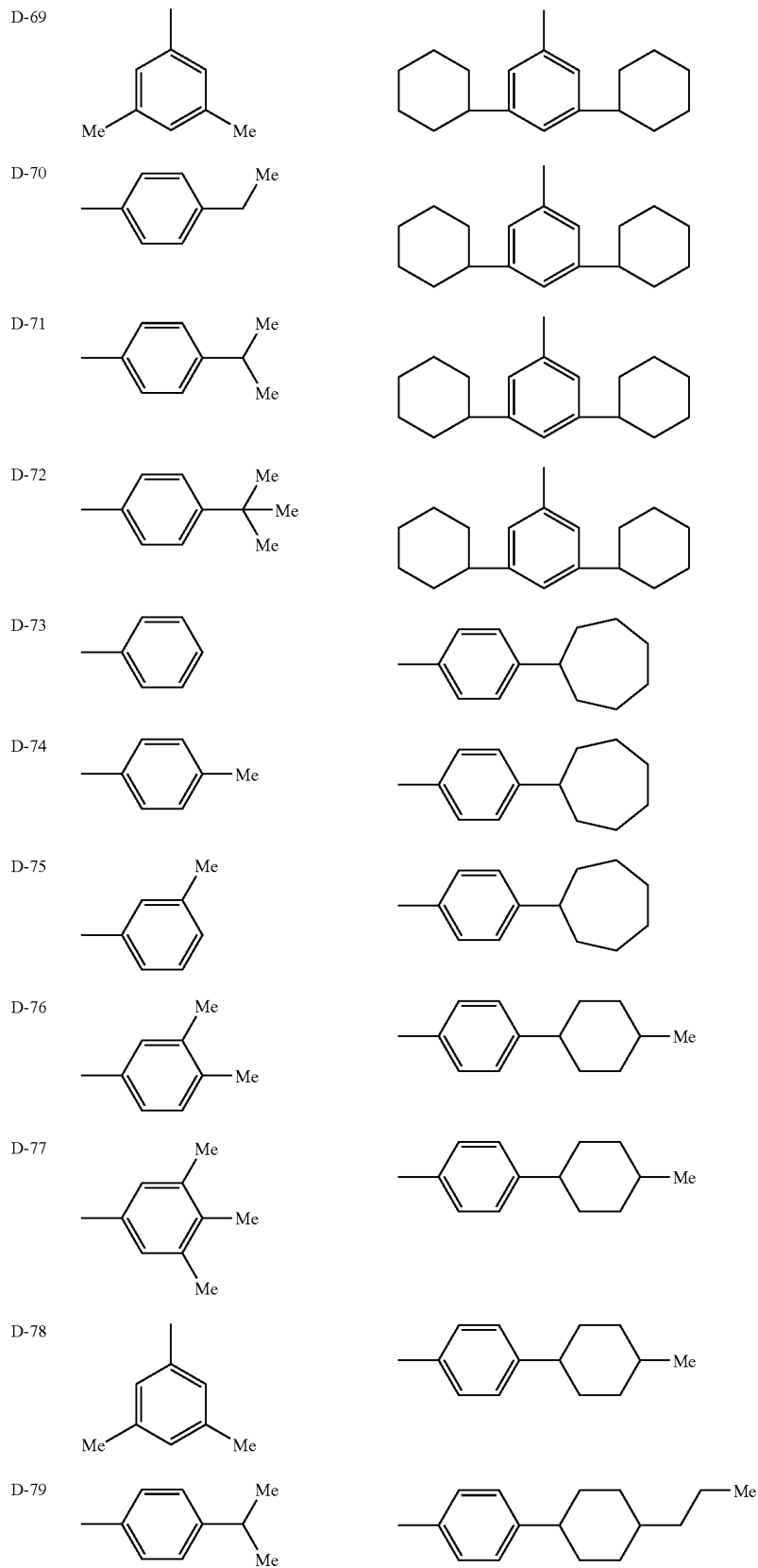

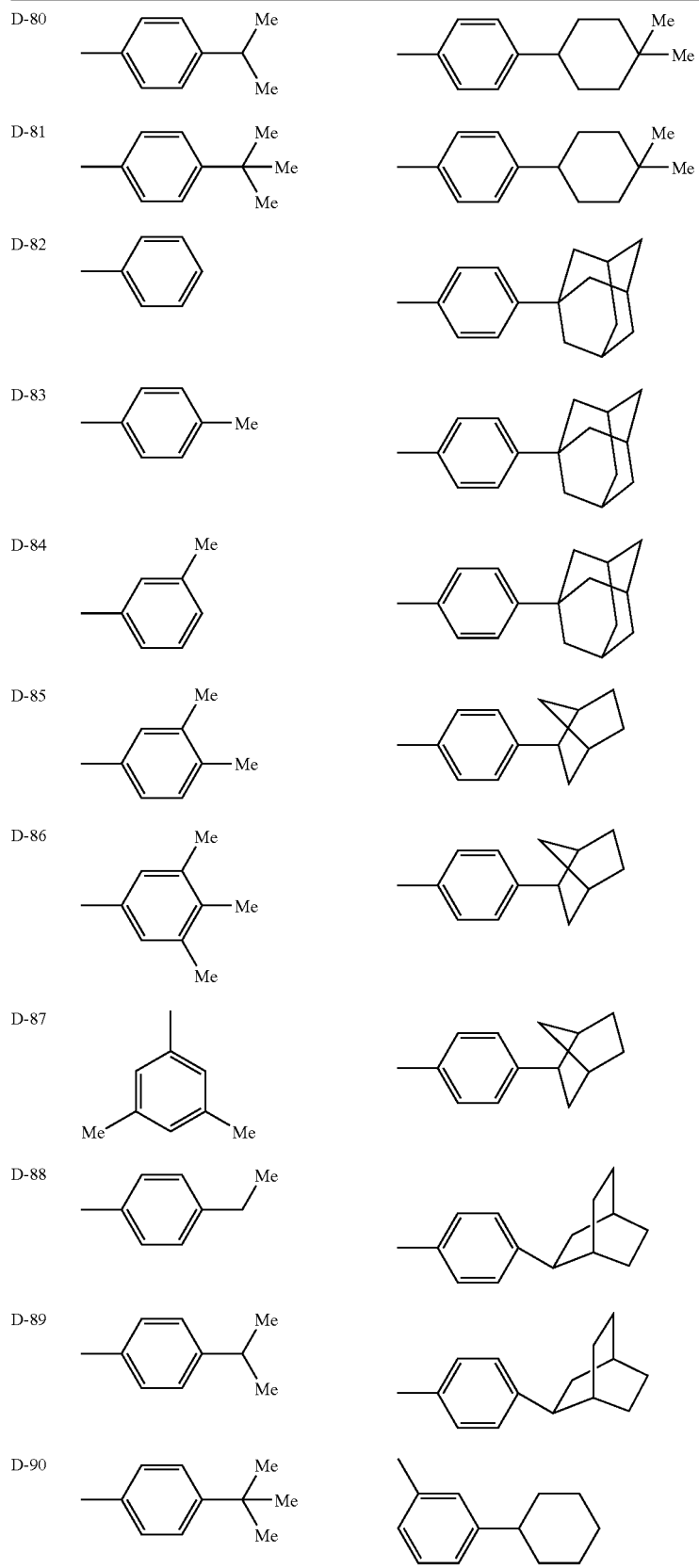

-continued
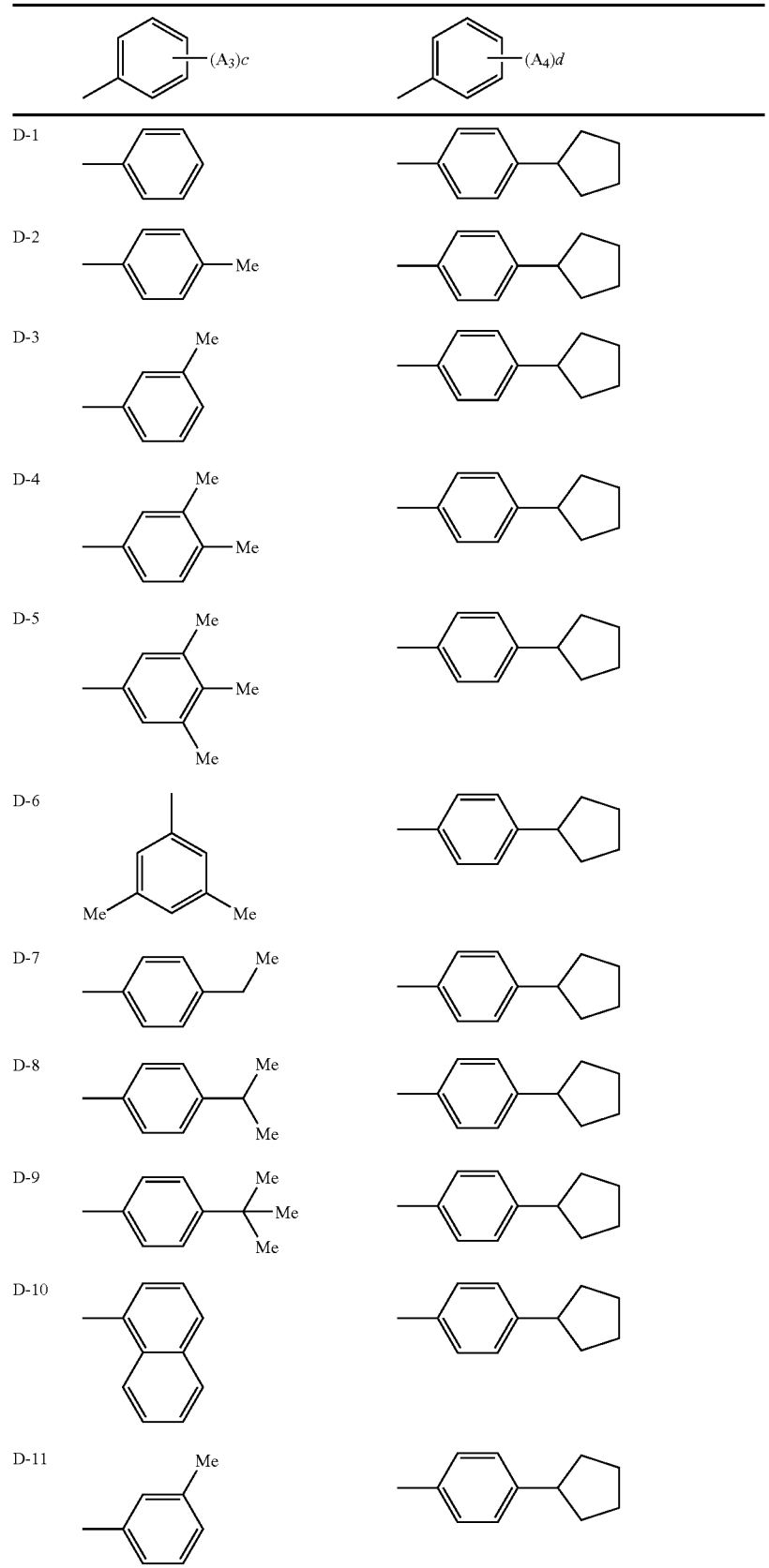

-continued
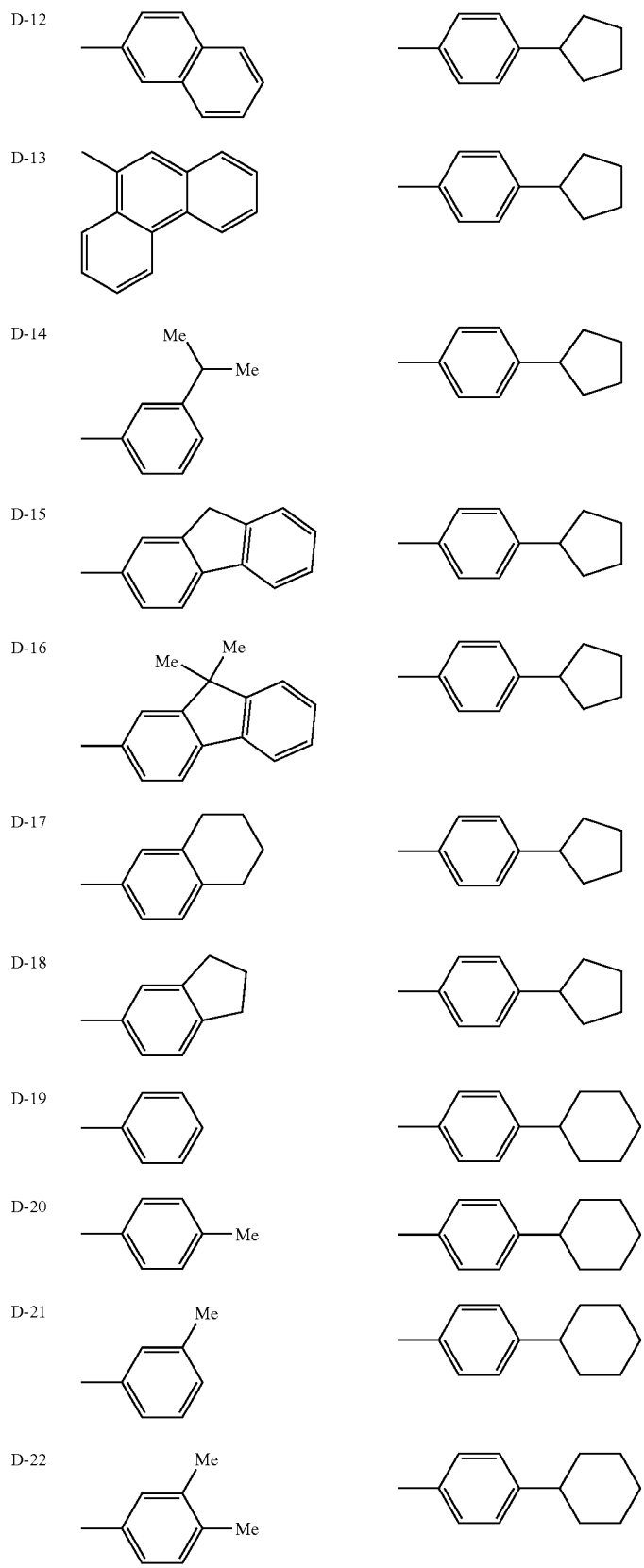

-continued
| | | |
|---|---|---|
| D-23 | 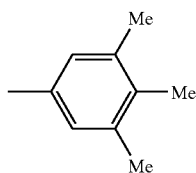 | 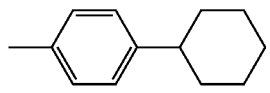 |
| D-24 | 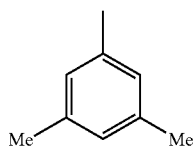 | 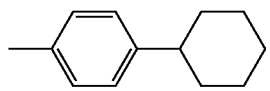 |
| D-25 | 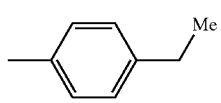 | 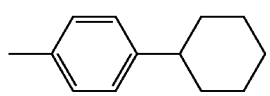 |
| D-26 | 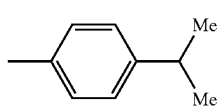 | 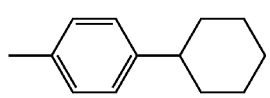 |
| D-27 | 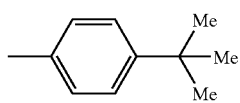 | 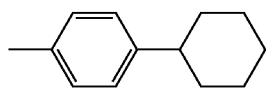 |
| D-28 | 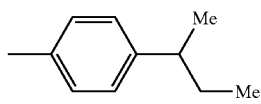 | 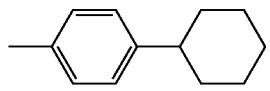 |
| D-29 | 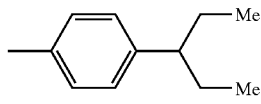 | 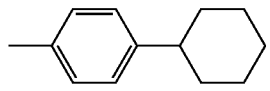 |
| D-30 | 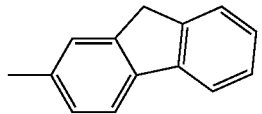 | 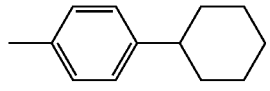 |
| D-31 | 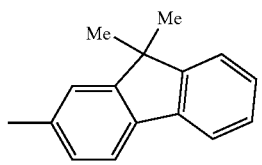 | 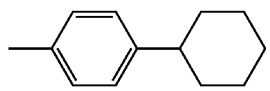 |
| D-32 | 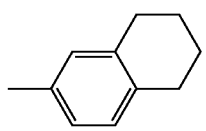 | 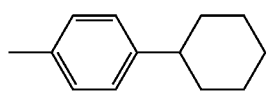 |
| D-33 | 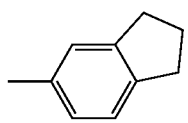 | 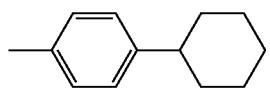 |
| D-34 | 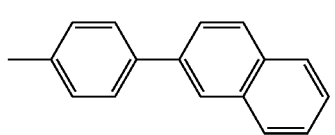 | 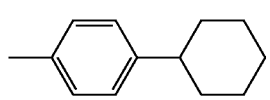 |

-continued
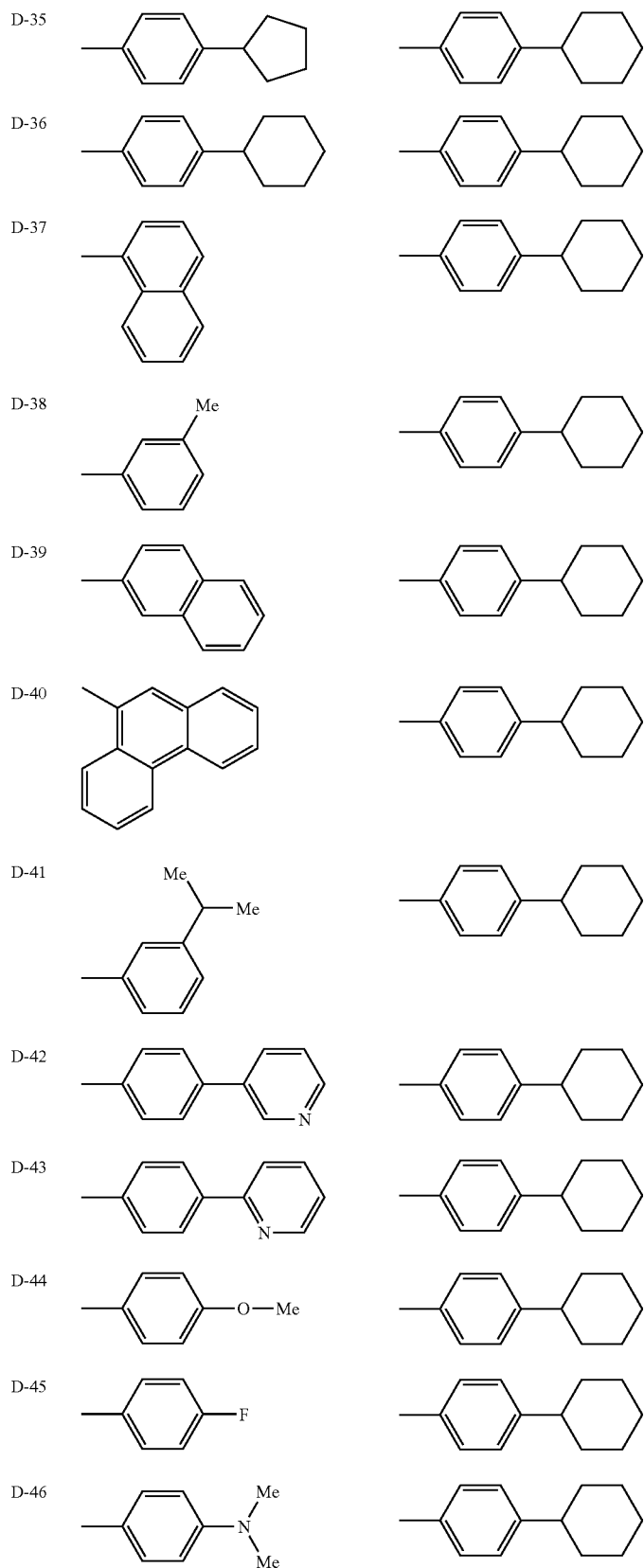

-continued
D-47 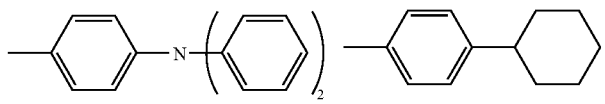
D-48 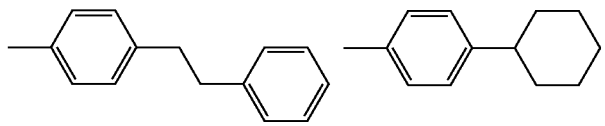
D-49 
D-50 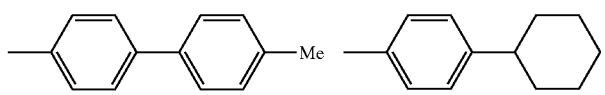
D-51 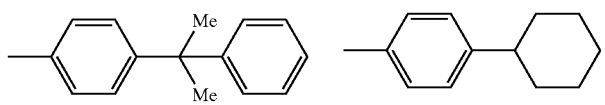
D-52 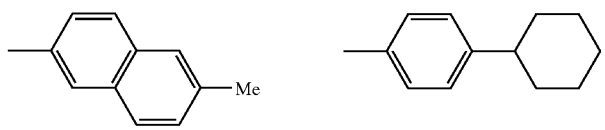
D-53 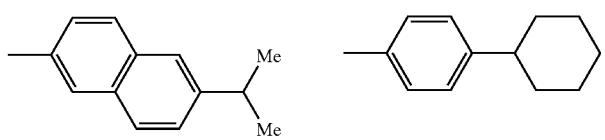
D-54 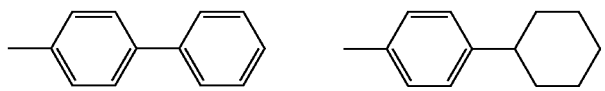
D-55 
D-56 
D-57 
D-58 

-continued
D-59 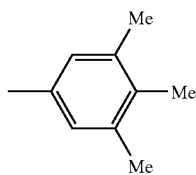 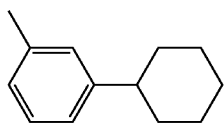
D-60 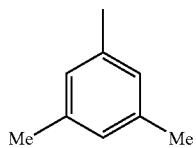 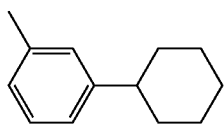
D-61 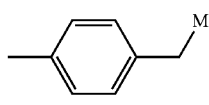 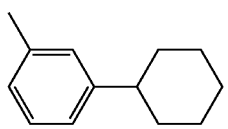
D-62 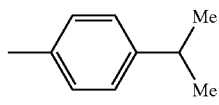 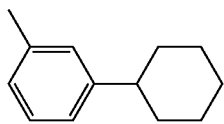
D-63 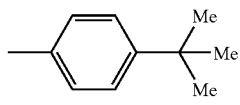 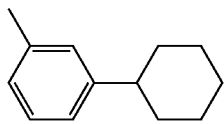
D-64 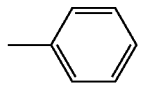 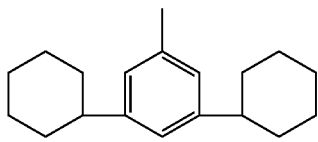
D-65 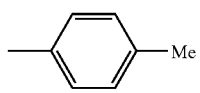 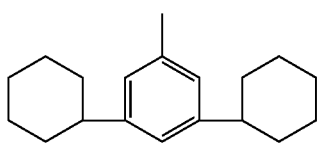
D-66 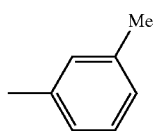 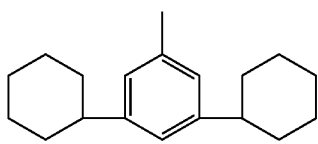
D-67 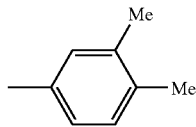 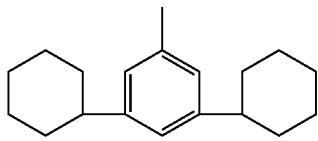
D-68 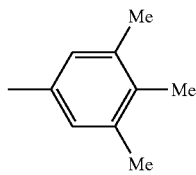 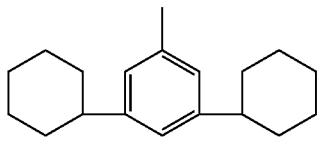

-continued
| | | |
|---|---|---|
| D-69 | 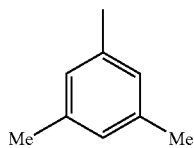 | 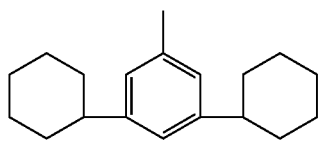 |
| D-70 | 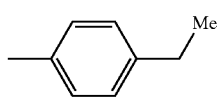 | 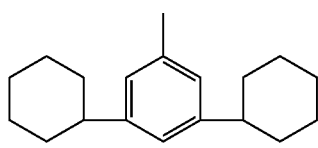 |
| D-71 | 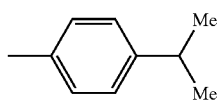 | 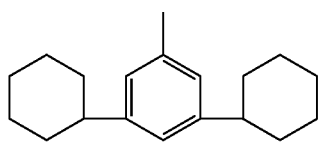 |
| D-72 | 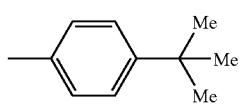 | 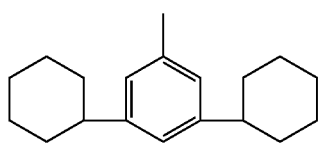 |
| D-73 | 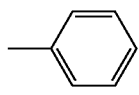 | 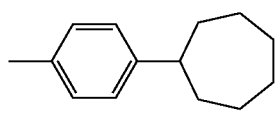 |
| D-74 | 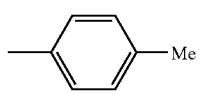 | 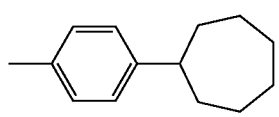 |
| D-75 | 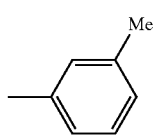 | 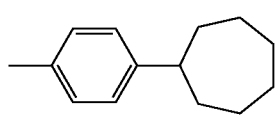 |
| D-76 | 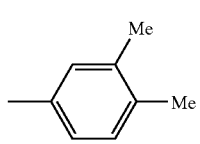 | 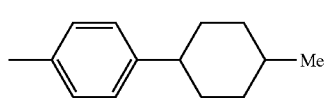 |
| D-77 | 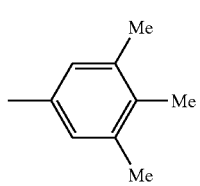 | 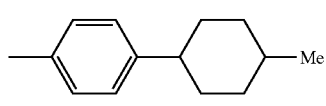 |
| D-78 | 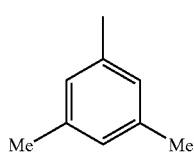 | 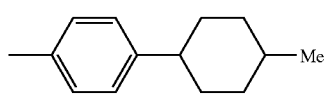 |
| D-79 | 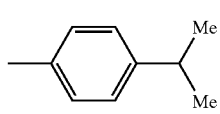 | 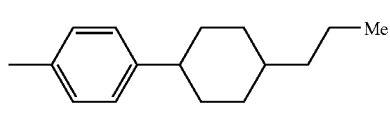 |

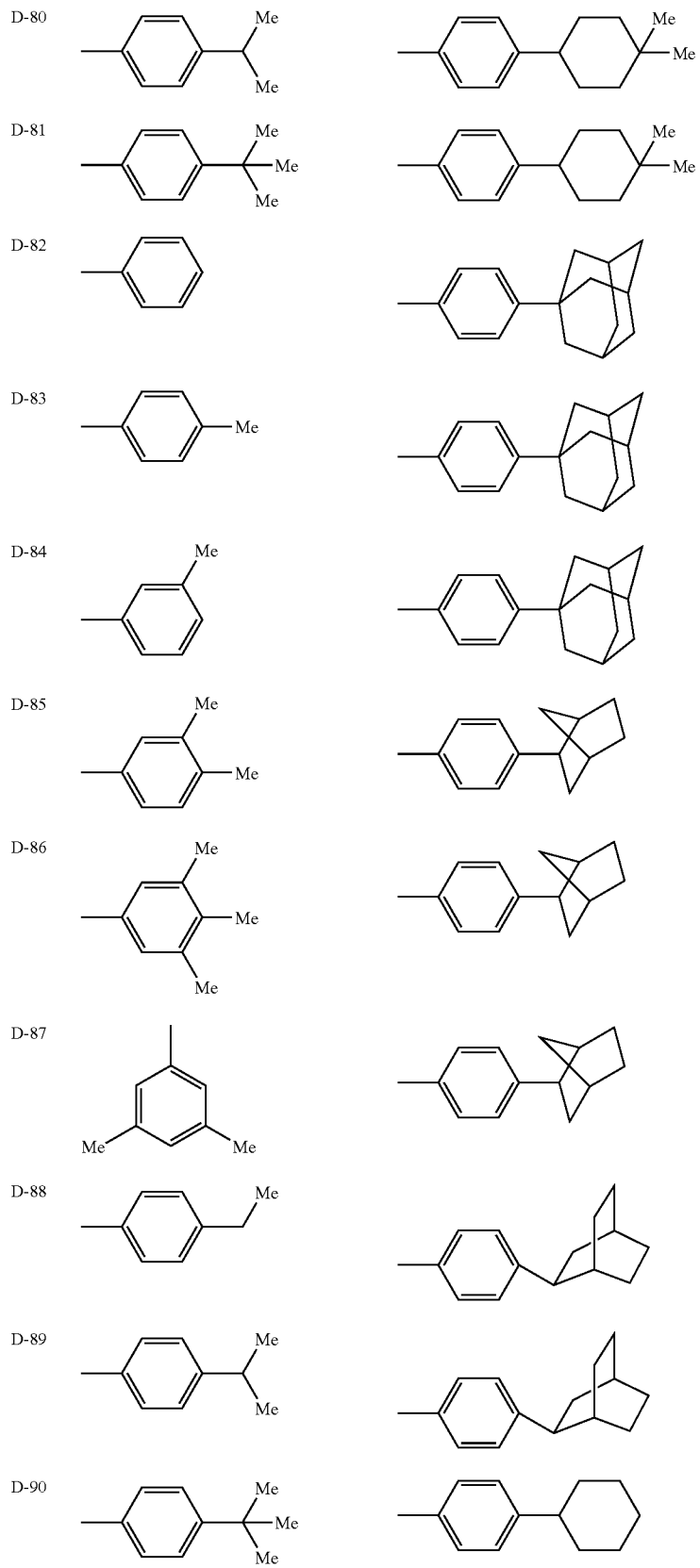

-continued
| | X₁ | X₂ |
|---|---|---|
| D-91 | 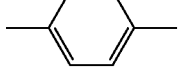 | 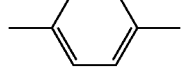 |
| D-92 | 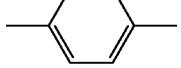 | 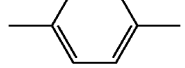 |
| D-93 | 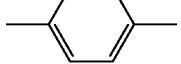 | 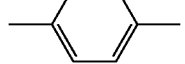 |
| D-94 | 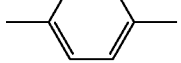 | 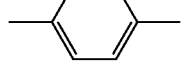 |
| D-95 | 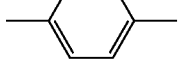 | 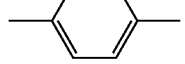 |
| D-96 | 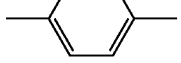 | 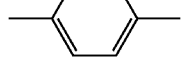 |
| D-97 | 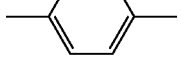 | 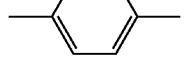 |
| D-98 | 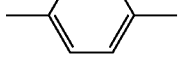 | 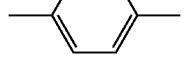 |
| D-99 | 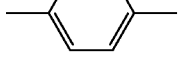 | 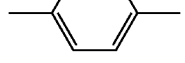 |
| D-100 | 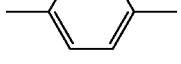 | 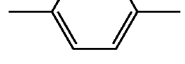 |
| D-101 | 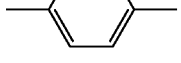 | 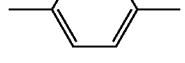 |
| D-102 | 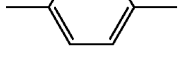 | 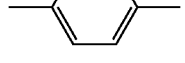 |
| D-103 | 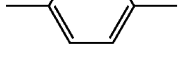 | 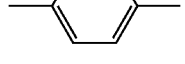 |
| D-104 | 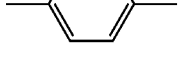 | 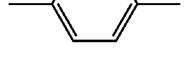 |
| D-105 | 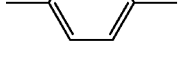 | 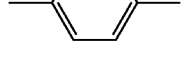 |
| D-106 | 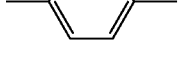 | 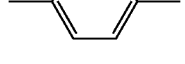 |

-continued
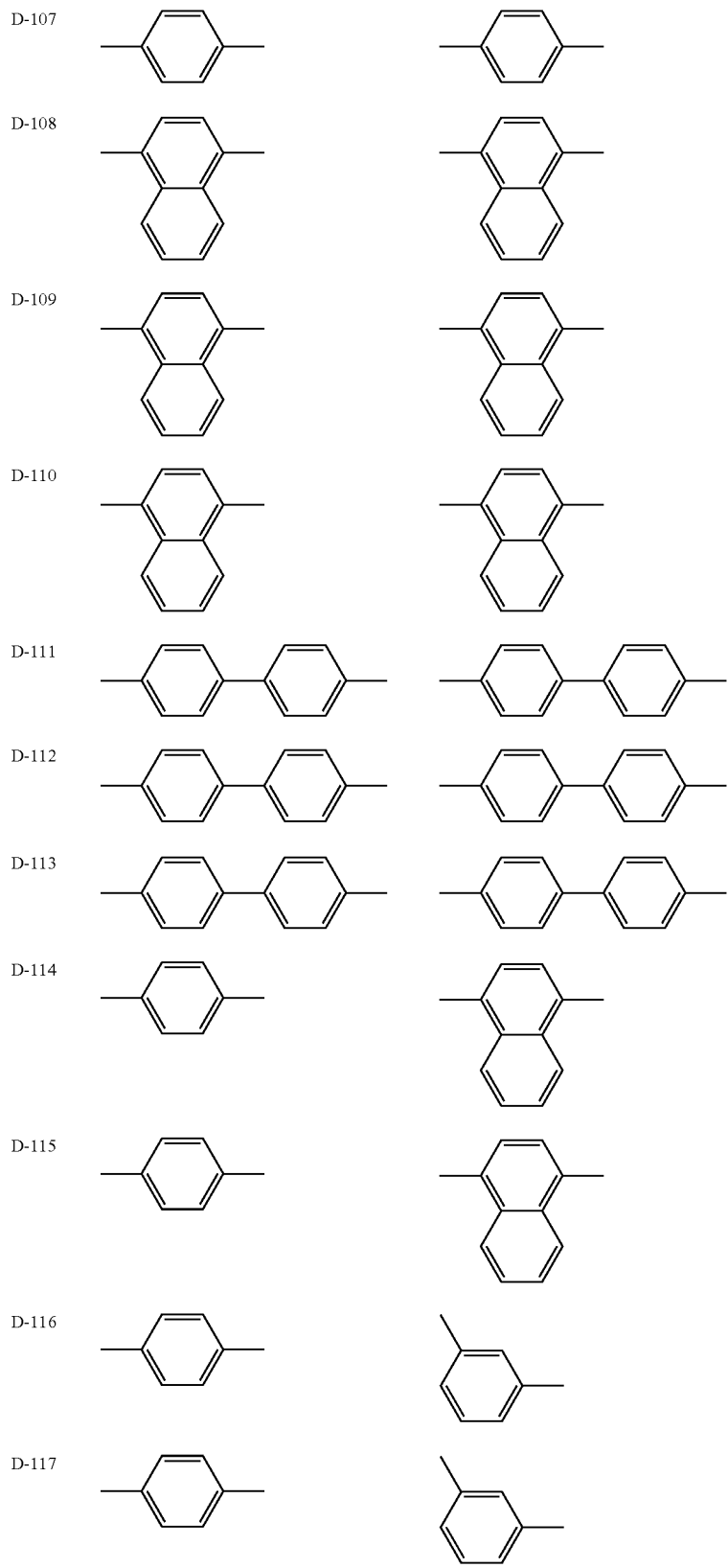

-continued
D-118 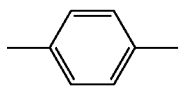 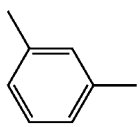
D-119 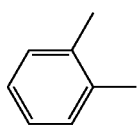 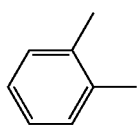
D-120 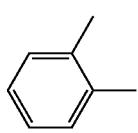 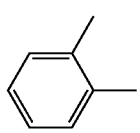
D-121 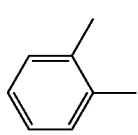 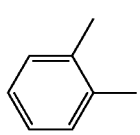
D-122 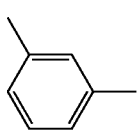 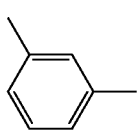
D-123 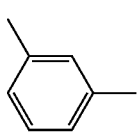 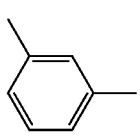
D-124 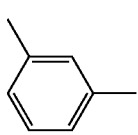 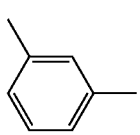
$-(A_5)e$ $-(A_6)f$
D-91 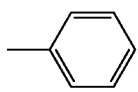
D-92 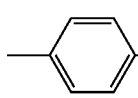 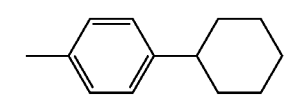
D-93 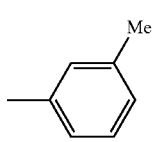 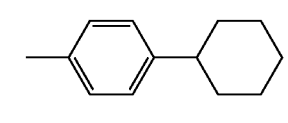
D-94 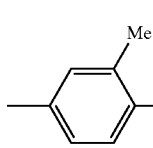 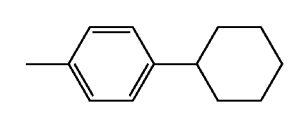

-continued
| | | |
|---|---|---|
| D-95 | 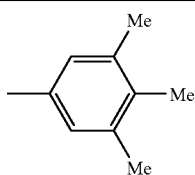 | 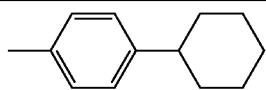 |
| D-96 | 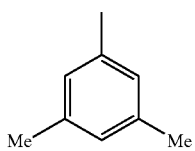 | 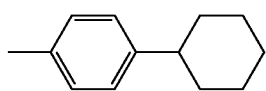 |
| D-97 | 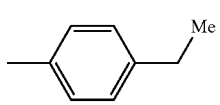 | 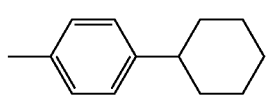 |
| D-98 | 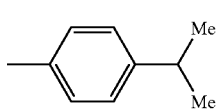 | 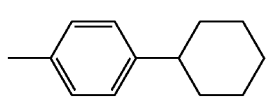 |
| D-99 | 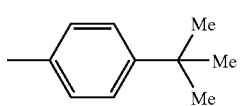 | 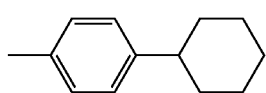 |
| D-100 | 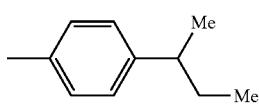 | 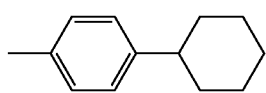 |
| D-101 | 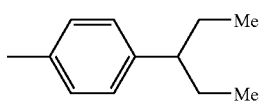 | 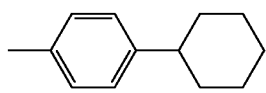 |
| D-102 | 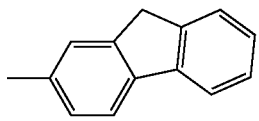 | 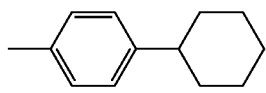 |
| D-103 | 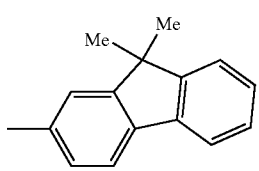 | 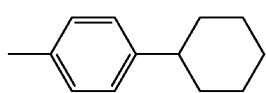 |
| D-104 | 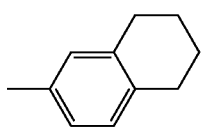 | 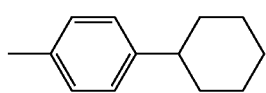 |
| D-105 | 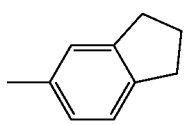 | 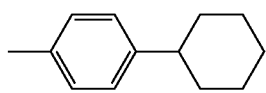 |
| D-106 | 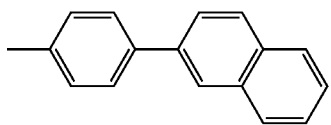 | 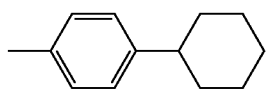 |

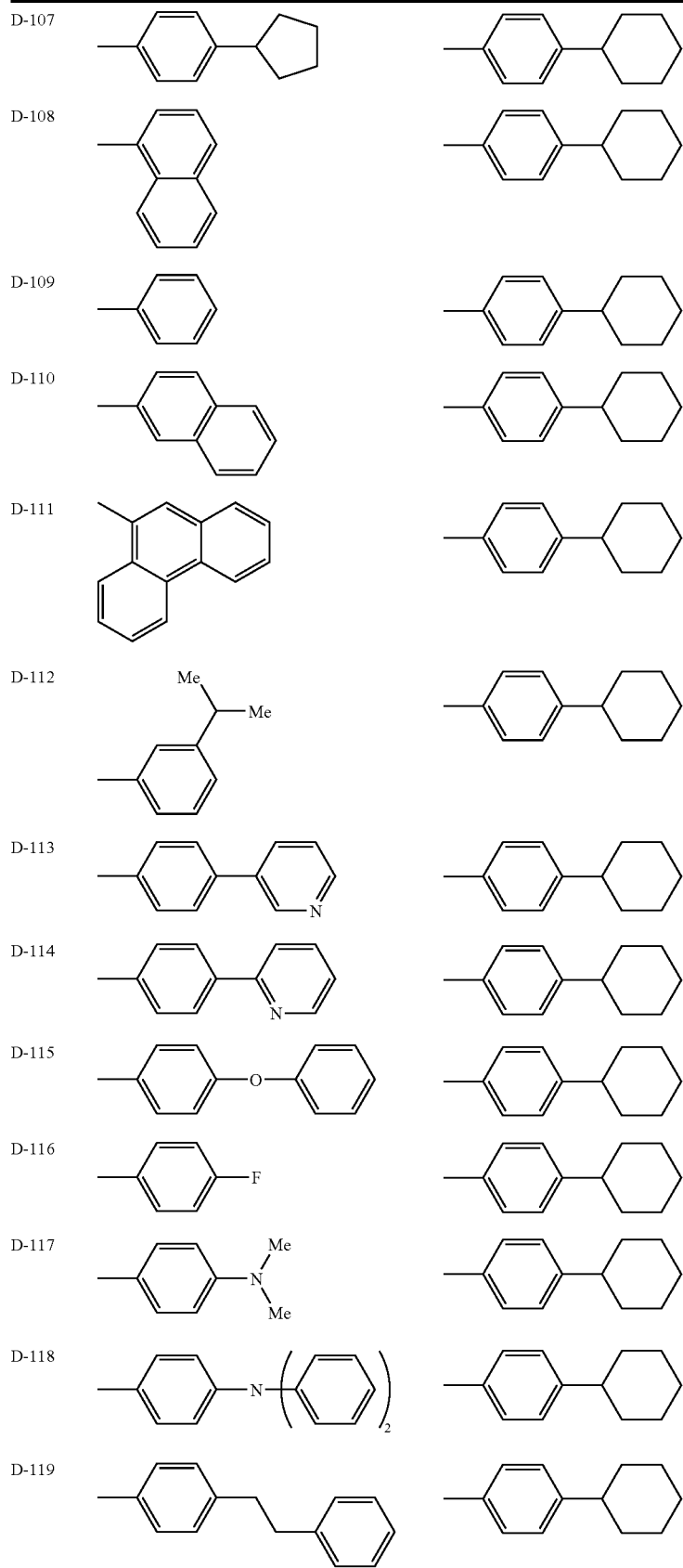

-continued
| | | |
|---|---|---|
| D-120 |  | |
| D-121 | 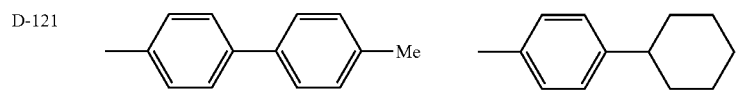 | |
| D-122 |  | |
| D-123 | 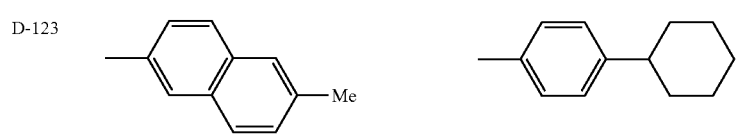 | |
| D-124 | 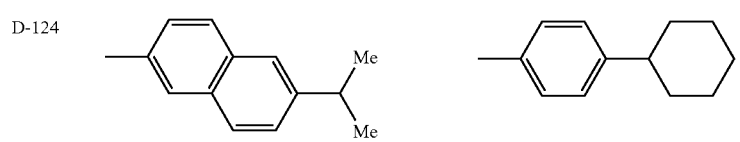 | |
| |  | |
| D-91 | 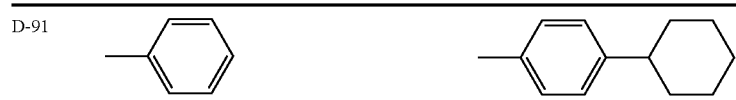 | |
| D-92 |  | |
| D-93 |  | |
| D-94 |  | |
| D-95 | 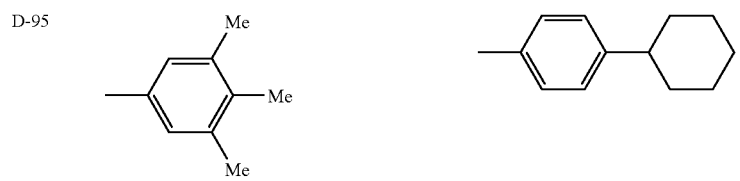 | |
| D-96 |  | |

-continued
| | | |
|---|---|---|
| D-97 | 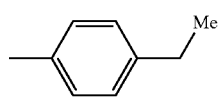 | 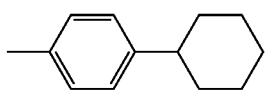 |
| D-98 | 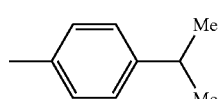 | 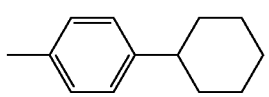 |
| D-99 | 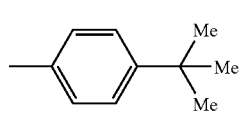 | 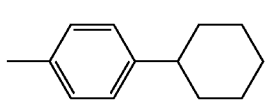 |
| D-100 | 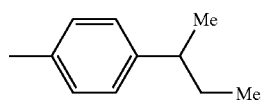 | 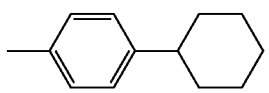 |
| D-101 | 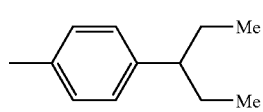 | 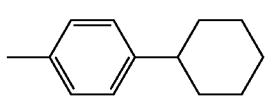 |
| D-102 | 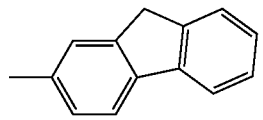 | 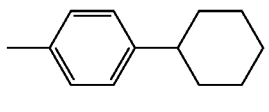 |
| D-103 | 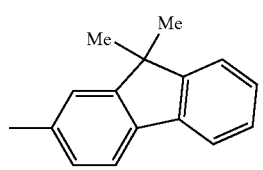 | 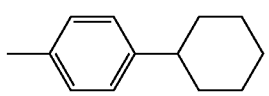 |
| D-104 | 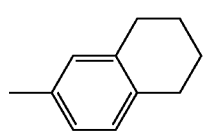 | 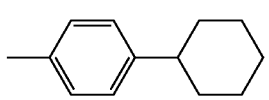 |
| D-105 | 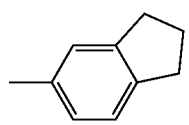 | 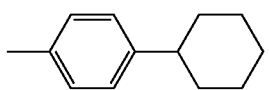 |
| D-106 | 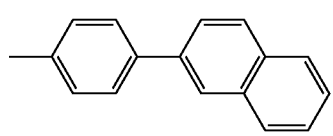 | 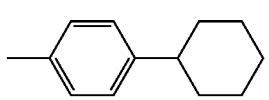 |
| D-107 | 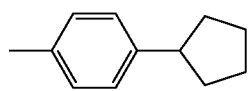 | 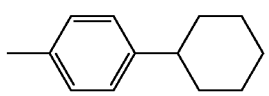 |
| D-108 | 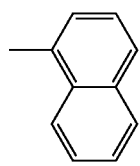 | 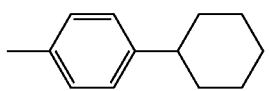 |

-continued
D-109 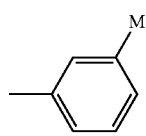 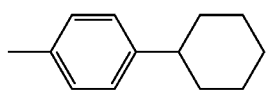
D-110 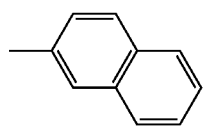 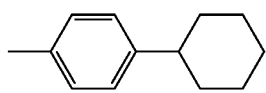
D-111 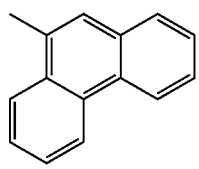 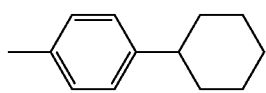
D-112 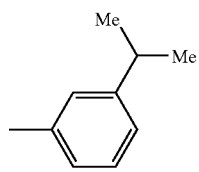 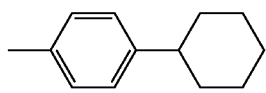
D-113 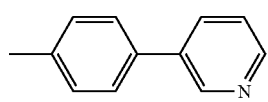 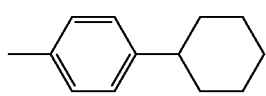
D-114 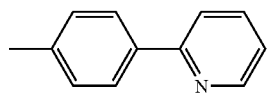 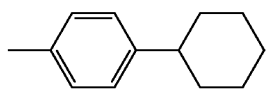
D-115 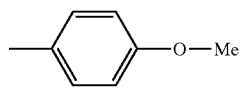 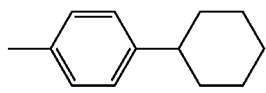
D-116  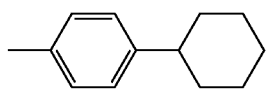
D-117 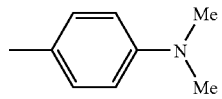 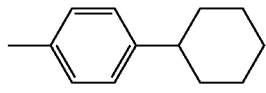
D-118 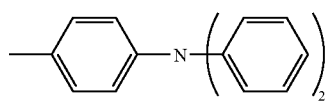 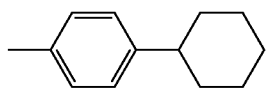
D-119 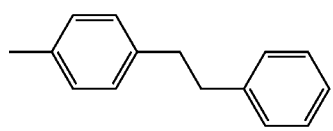 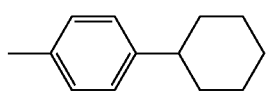
D-120 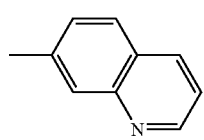 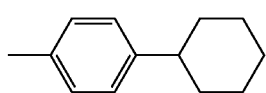

-continued

D-121 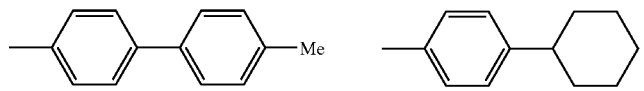

D-122 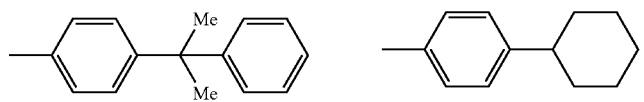

D-123 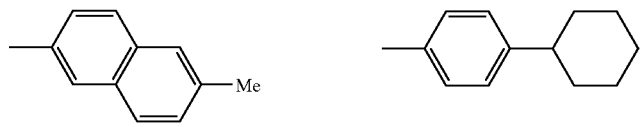

D-124 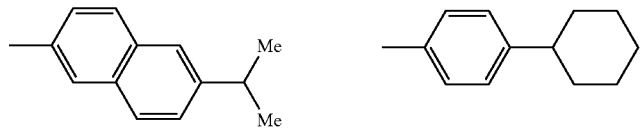

Following is a description regarding a preparing process about the aromatic amine derivative of the present invention.

The preparation process of the aromatic amine derivative represented by general formula (1) of the present invention is not particularly limited and may be in accordance with well-known process, for example, amination of 6,12-dibromochrysene obtained in accordance with a description on Rev. Roum. Chim., 34 1907 (1989) (M. D. Bancia) with the use of diaryl amine prepares the aromatic amine.

Further, the preparation process of the aromatic amine derivative represented by general formula (2) of the present invention is not particularly limited and may be in accordance with well-known process, for example, coupling reaction between 6,12-dibromo chrysene and triarylamino boronic acid prepares the aromatic amine.

In the aromatic amine derivative represented by the general formula (1) or (2) of the present invention, since the substituted benzene ring is connected to a diaminocrysene structure as a light emission center, the association between the compounds is prevented, resulting in a prolonged lifetime thereof. Further, in an occasion that a cycloalkyl group connects to an end benzene ring coupling with a nitrogen atom, the association between the compounds is further prevented resulting in an enhancement of the prolonged lifetime. Moreover, the aromatic amine derivative of the present invention has strong fluorescent property in its solid state, superior electroluminescent property and further fluorescent quantum efficiency of 0.3 or greater. Furthermore, because the aromatic amine derivative of the present invention has a superior injecting property and a superior hole transporting property from the metal electrode or from the organic thin film layer together with a superior electron injecting property and a superior electron transporting property from the metal electrode or from the organic thin film layer, it is effectively employed as a light emitting material, particularly as a dopant for the organic EL devices; and still further, it may be employed as another hole transporting material, electron transporting material or a dopant.

The organic EL device of the present invention is a device comprising a film of organic compounds having a single layer or a plurality of layers disposed between an anode and a cathode. When the film of organic compounds has a single layer, a light emitting layer is disposed between the anode and the cathode. The light emitting layer contains the light emitting material and may further contain a hole injecting material and an electron injecting material in order to effectively transport holes injected from the anode or electrons injected from the cathode to the light emitting material. The aromatic amine derivatives represented by the general formula (1) or the general formula (2) has an enhanced light emitting property and excellent hole injecting ability and hole transporting ability as well as excellent electron injecting ability and electron transporting ability and, therefore, can be used as a light emitting material in the light emitting layer.

In the organic EL device of the present invention, the light emitting layer contains the aromatic amine derivative of the present invention in an amount of preferably 0.1 to 20% by weight and more preferably 1 to 10% by weight. Further, the aromatic amine derivatives of the present invention exhibit not only an extremely high fluorescent quantum efficiency but also high hole transporting ability and electron transporting ability, and further are capable of forming a uniform thin film, so that the light emitting layer may be formed from the aromatic amine derivatives only.

On the other hand, in the case where the organic EL device of the present invention includes two or more organic thin film layers having at least the light emitting layer which are sandwiched between the cathode and anode, the organic thin film layers preferably include an organic layer containing the aromatic amine derivative of the present invention as an essential component which is provided between the anode and the light emitting layer. Such an organic layer may be a hole injecting layer, a hole transporting layer, etc.

Further, in a case where the aromatic amine derivative of the present invention is employed as a doping material, it is preferable that at least one kind selected from the group consisting of anthracene derivatives of a following general formula (5), anthracene derivatives of a following general formula (6) and pyrene derivatives of a following general formula (7) is employed as a host material.

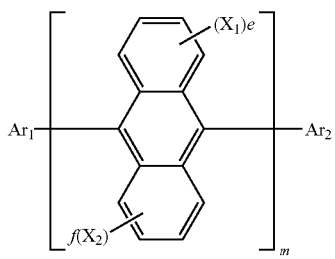

(3)

In the general formula (3), $X_1$ and $X_2$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 1 to 50 ring carbon atoms, a substituted or unsubstituted cycloalkyl group having 3 to 50 ring carbon atoms, a substituted or unsubstituted alkoxyl group having 1 to 50 ring carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 3 to 50 ring carbon atoms or a halogen atom; e and f each independently represents an integer of 0 to 4; when e and f are 2 or greater, $X_1$ and $X_2$ may be the same with or different from each other.

$Ar_1$ and $Ar_2$ each independently represents a substituted or unsubstituted aryl group having 5 to 50 ring carbon atoms or a substituted or unsubstituted heterocyclic group having 3 to 50 ring carbon atoms; at least one of $Ar_1$ or $Ar_2$ represents a substituted or unsubstituted aryl group with a condensed ring and having 10 to 50 ring carbon atoms; and m represents an integer of 1 to 3.

When m is 2 or greater, a group within a parentheses: [ ] may be the same with or different from each other.

Specific examples and substituents of the $X_1$, $X_2$, $Ar_1$ and $Ar_2$ are the same as those explained about the foregoing general formula (1).

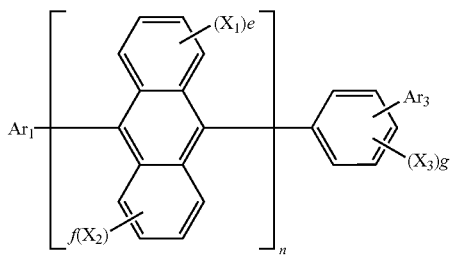

(4)

In the general formula (4), $X_1$ to $X_2$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 1 to 50 ring carbon atoms, a substituted or unsubstituted cycloalkyl group having 3 to 50 ring carbon atoms, a substituted or unsubstituted alkoxyl group having 1 to 50 ring carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 3 to 50 ring carbon atoms or a halogen atom; e, f, and g each independently represents an integer of 0 to 4; when e, f, and g are 2 or greater, $X_1$, $X_2$ and $X_3$ may be the same with or different from each other.

$Ar_1$ represents a substituted or unsubstituted aryl group with a condensed ring and having 10 to 50 ring carbon atoms and $Ar_3$ represents substituted or unsubstituted aryl group having 5 to 50 ring carbon atoms.

n represents an integer of 1 to 3; when n is 2 or greater, a group within a parentheses: [ ] may be the same with or different from each other.

Specific examples and substituents of the $X_1$ to $X_3$, $Ar_1$ and $Ar_3$ are the same as those explained about the foregoing general formula (1).

Specific examples of anthracene derivative represented by the general formulae (3) and (4) will be shown below, though not particularly limited thereto.

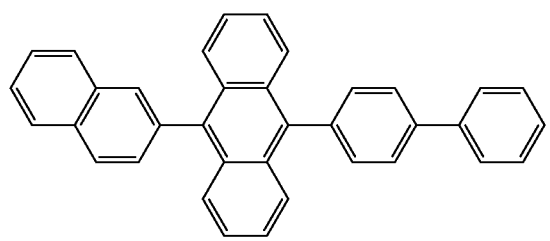

AN1

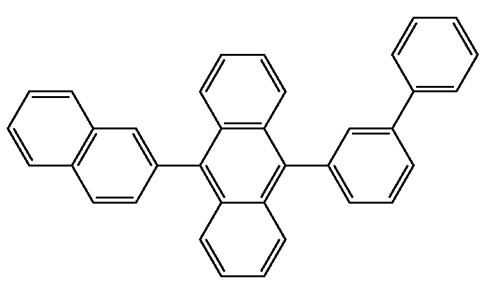

AN2

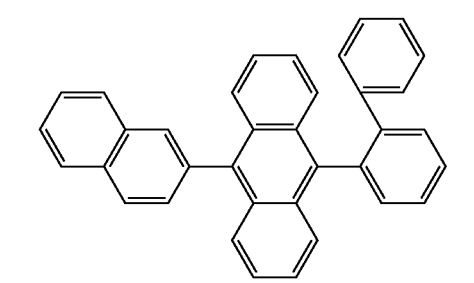

AN3

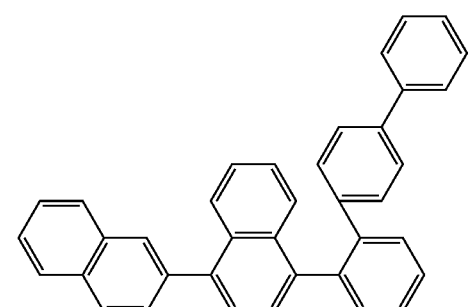

AN4

-continued
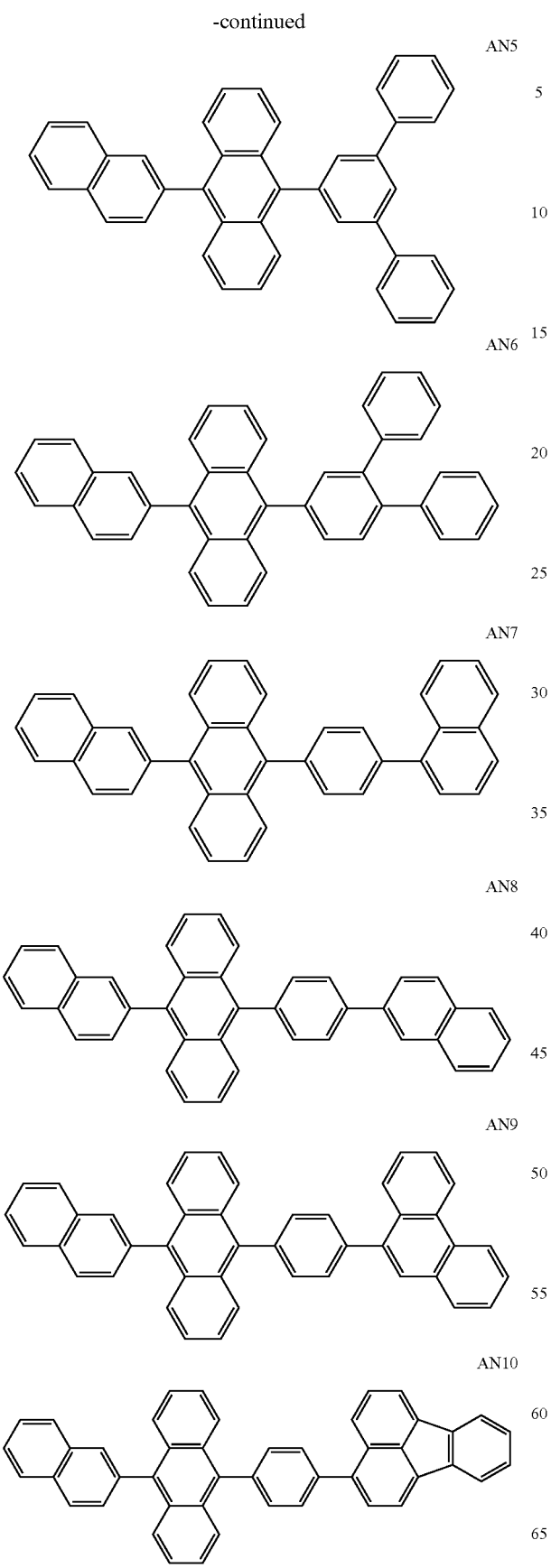
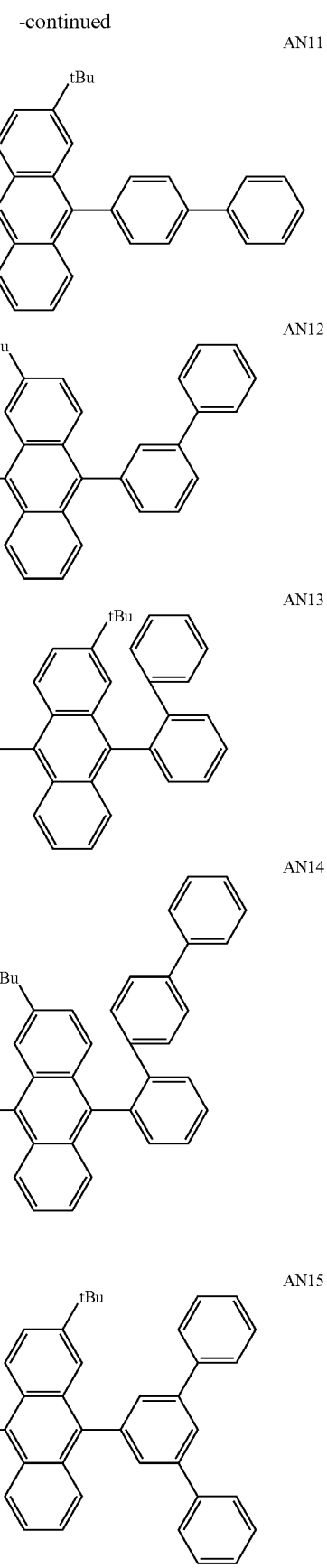

-continued
AN16
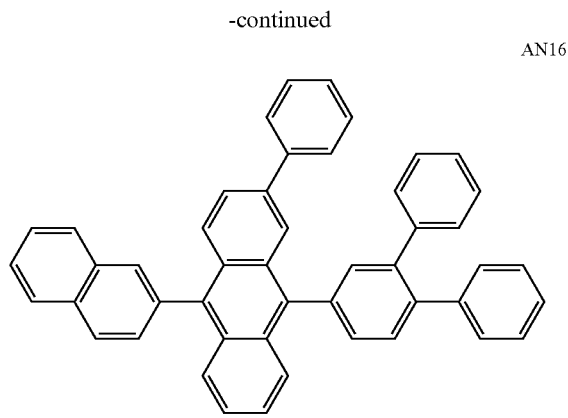
AN17
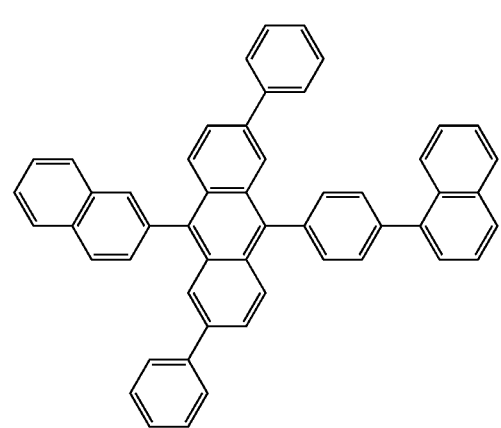
AN18
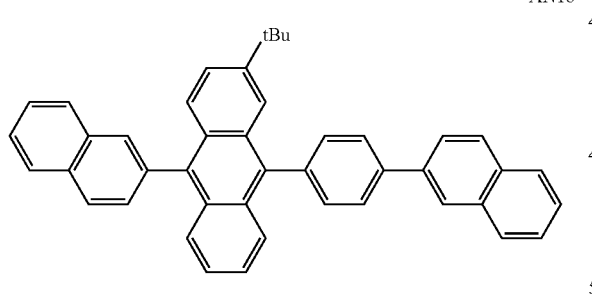
AN19
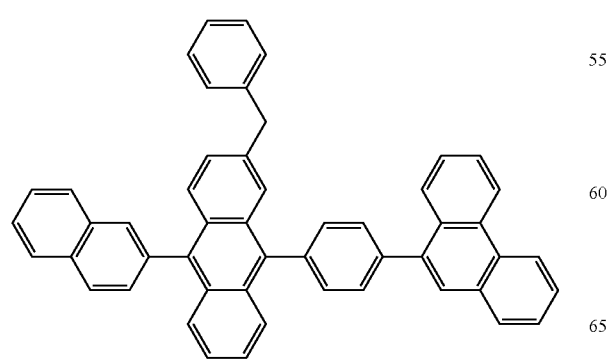
-continued
AN20
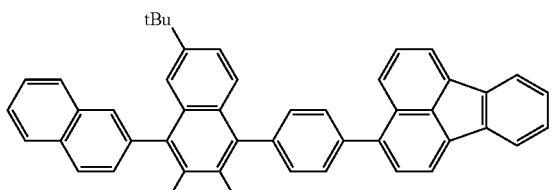
AN21
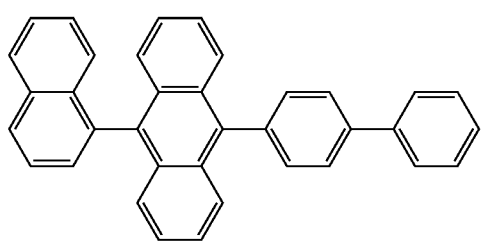
AN22
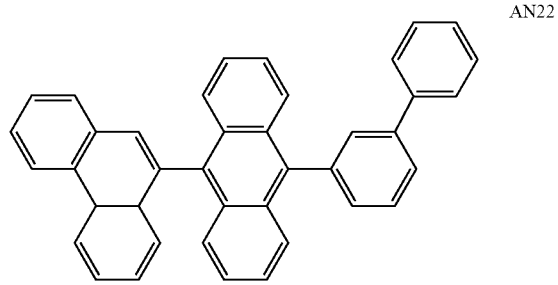
AN23
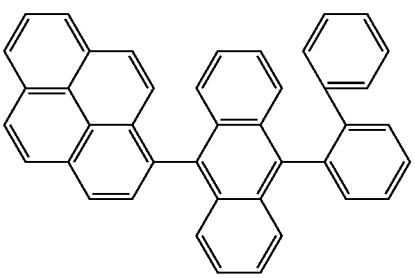
AN24
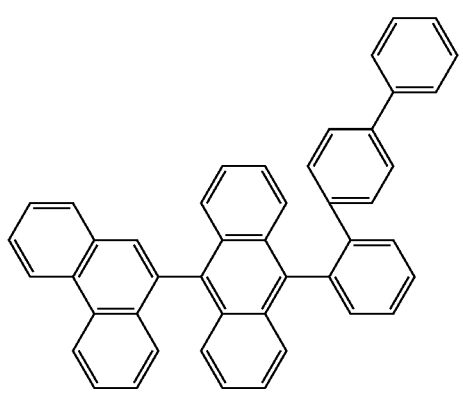

-continued
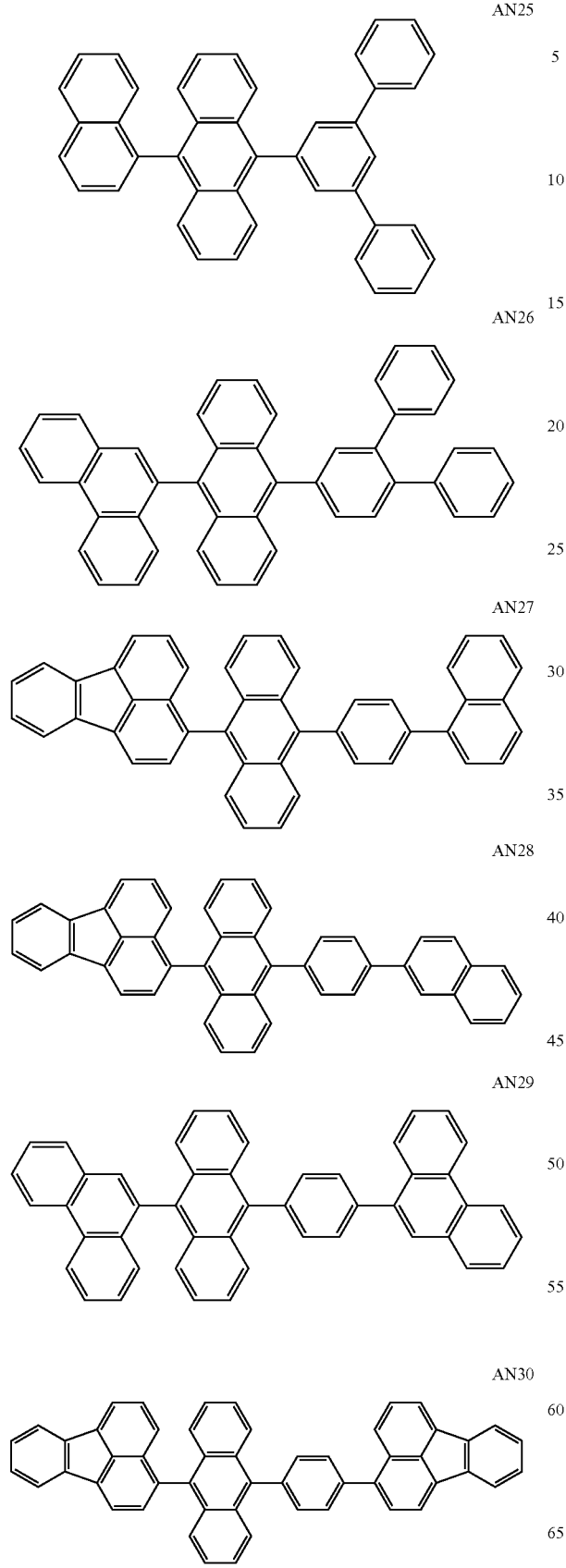
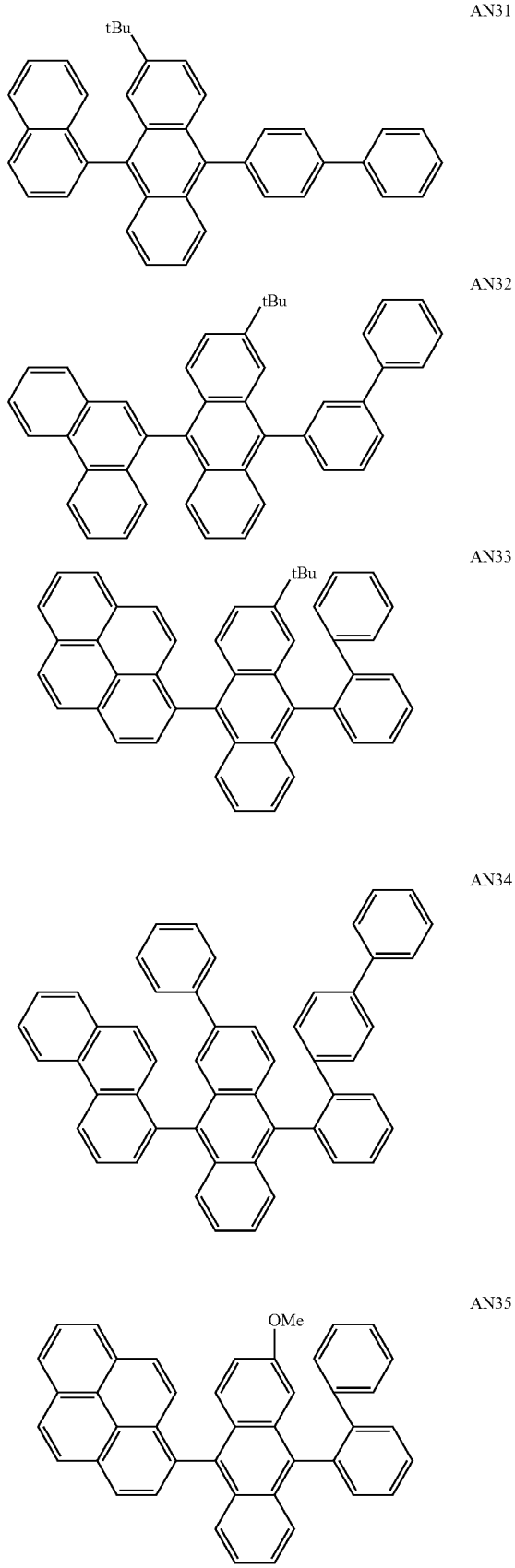

-continued
AN36
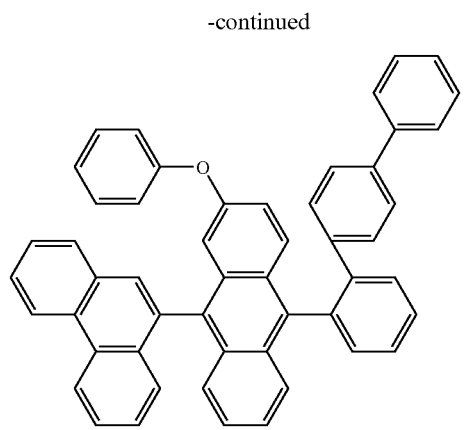
AN37
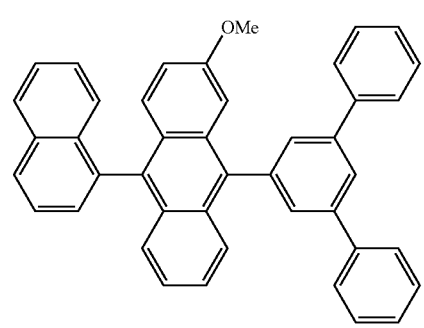
AN38
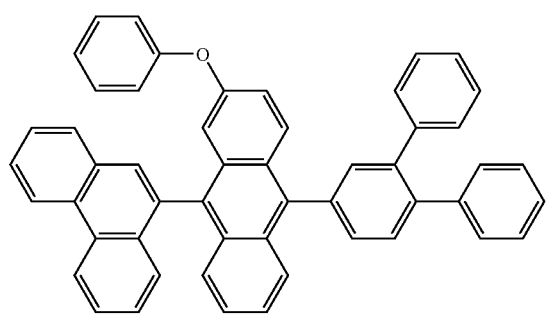
AN39
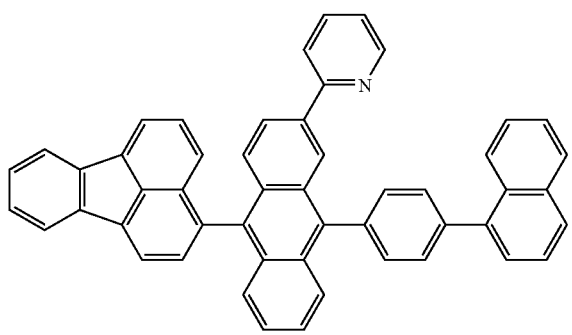
-continued
AN40
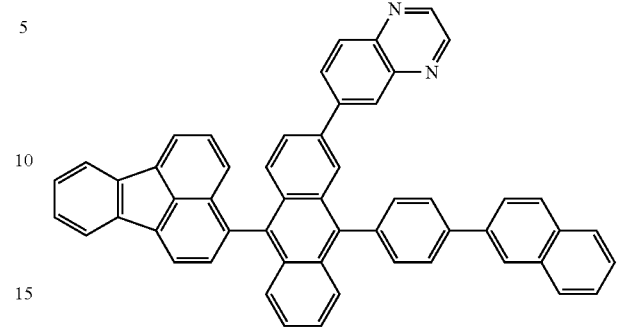
AN41
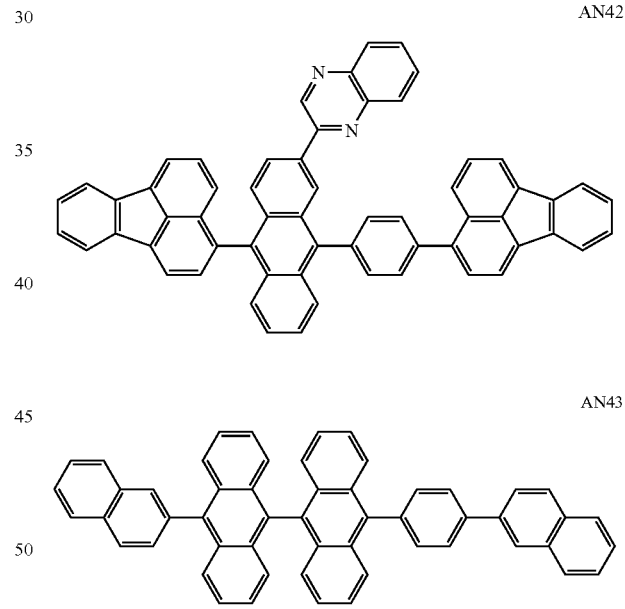
AN42
AN43
AN44
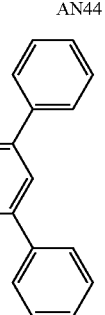

-continued

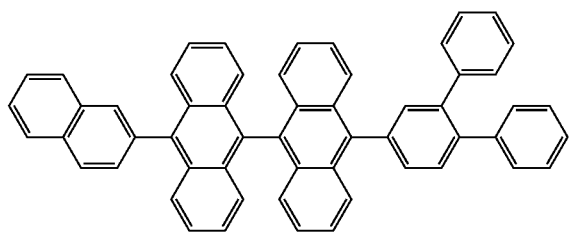
AN45

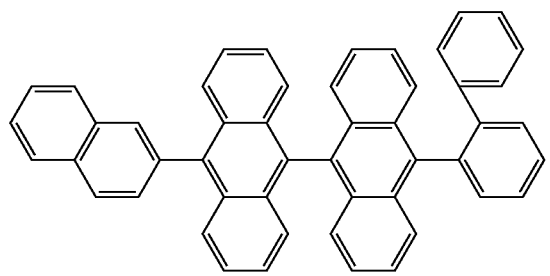
AN46

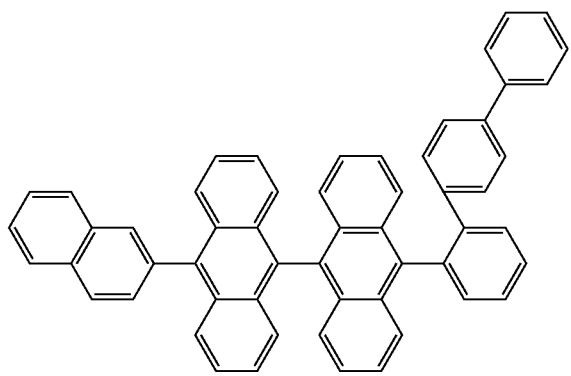
AN47

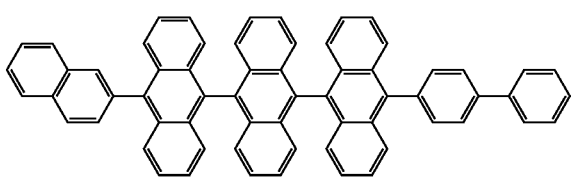
AN48

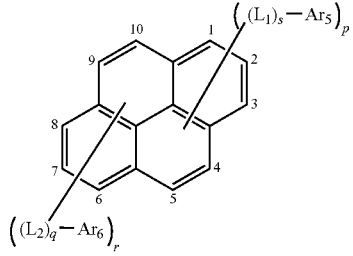
(5)

In the general formula (5), $Ar_5$ and $Ar_6$ each represents a substituted or unsubstituted aryl group having 6 to 50 ring carbon atoms;

$L_1$ and $L_2$ each represents a substituted or unsubstituted phenylene group, a substituted or unsubstituted naphthalenylene group, a substituted or unsubstituted fluorenylene group or a substituted or unsubstituted dibenzosilolylene group;

s represents an integer of 0 to 2, p represents an integer of 1 to 4, q represents an integer of 0 to 2 and r represents an integer of 0 to 4; and, $L_1$ or $Ar_5$ bonds to any one of 1 to 5 position of pyrene, also $L_2$ or $Ar_6$ bonds to any one of 6 to 10 position thereof;

however, when p+r is an even number, $Ar_5$, $Ar_6$, $L_1$ and $L_2$ satisfy a following requirement (1) or a requirement (2):

(1) $Ar_5 \neq Ar_6$ and/or $L_1 \neq L_2$ (wherein ≠ means that each group has a different structure)

(2) when $Ar_5 = Ar_6$ and $L_1 = L_2$ (2-1) s≠q and/or p≠r, or (2-2) when s=q and p=r, (2-2-1) both $L_1$ and $L_2$ or pyrene each bonds respectively to different positions of $Ar_5$ and $Ar_6$, or (2-2-2) both $L_1$ and $L_2$ or pyrene each bonds respectively to the same position of $Ar_5$ and $Ar_6$, excluding a case where a pyrene derivative having both $L_1$ and $L_2$ or both $Ar_5$ and $Ar_6$ bond to 1 and 6 positions thereof, or 2 and 7 positions thereof.

Specific examples and substituents of the $Ar_5$, $Ar_6$, $L_1$ and $L_2$ are the same as those explained about the foregoing general formula (1).

Specific examples of the pyrene derivative represented by the general formula (5) will be shown below, though not particularly limited thereto.

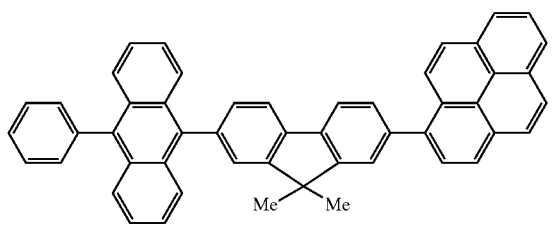
P1

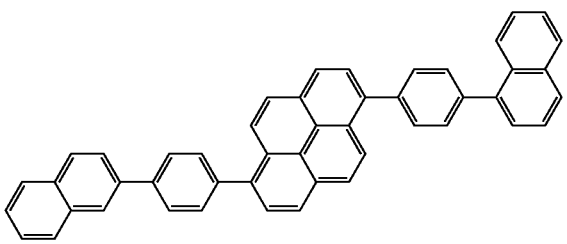
P2

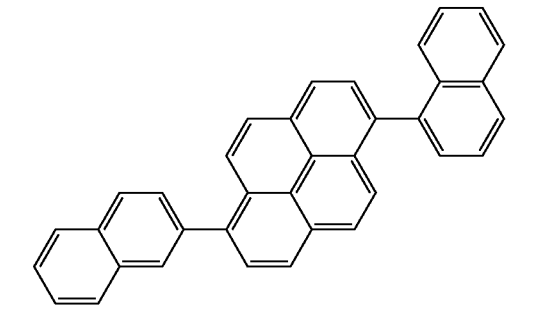
P3

P4
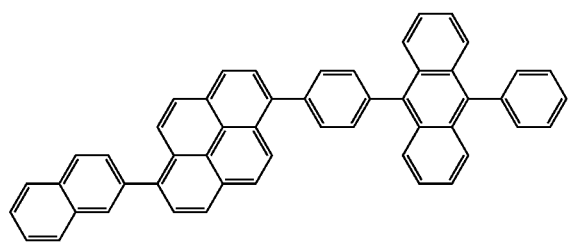
P5
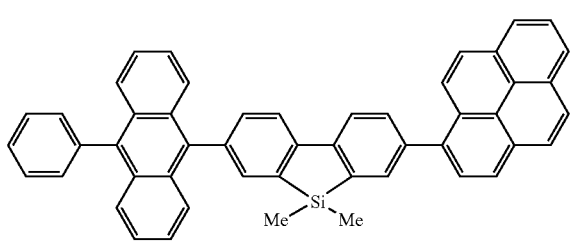
P6
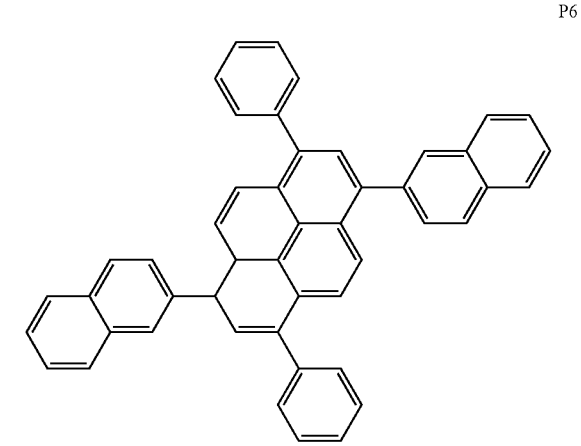
P7
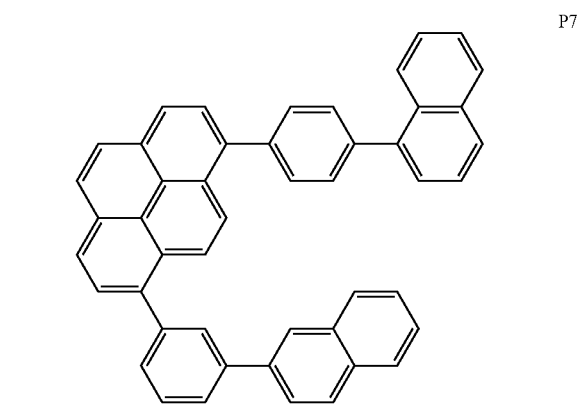
P8
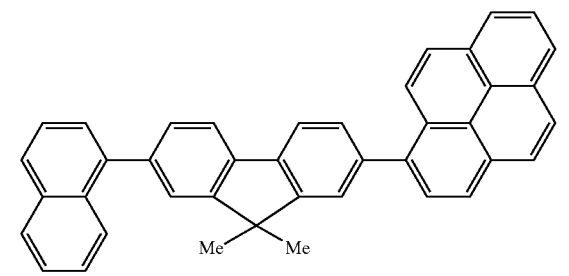
P9
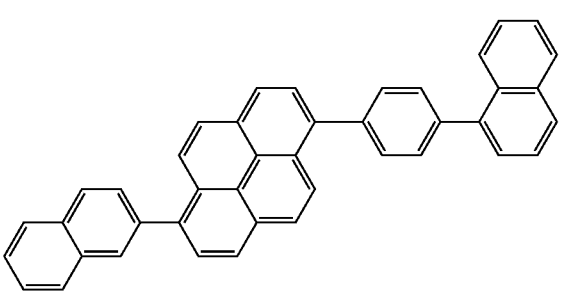
P10
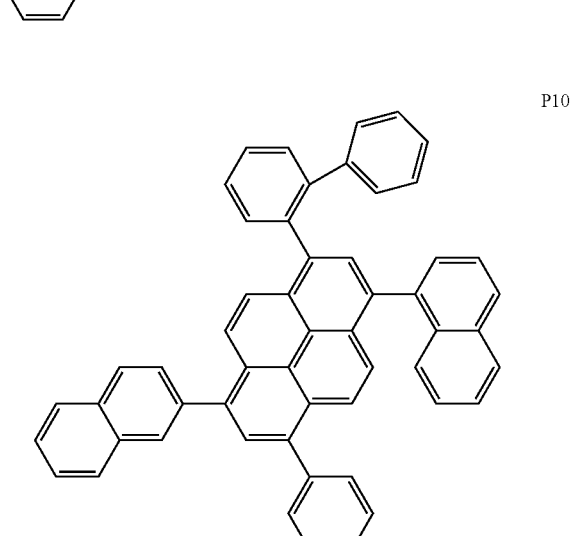
P11
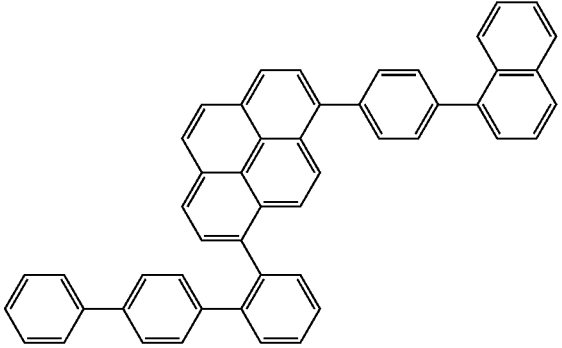
P12
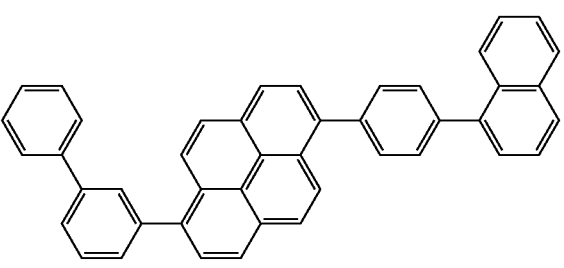

-continued

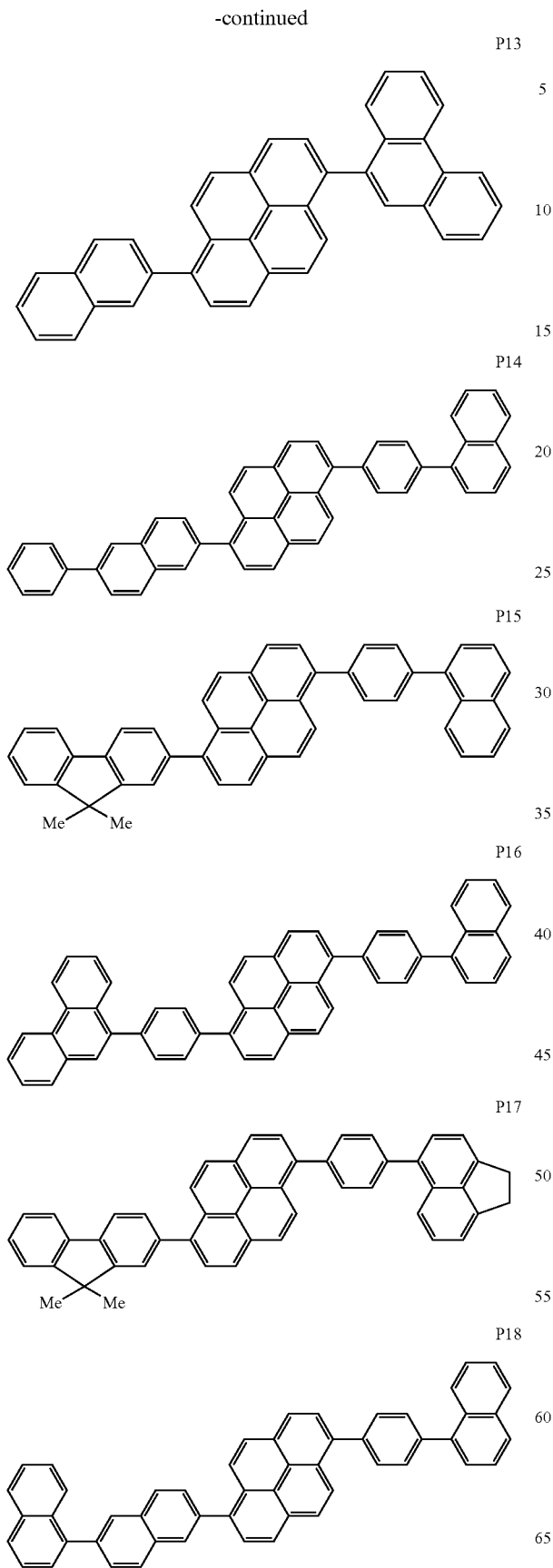

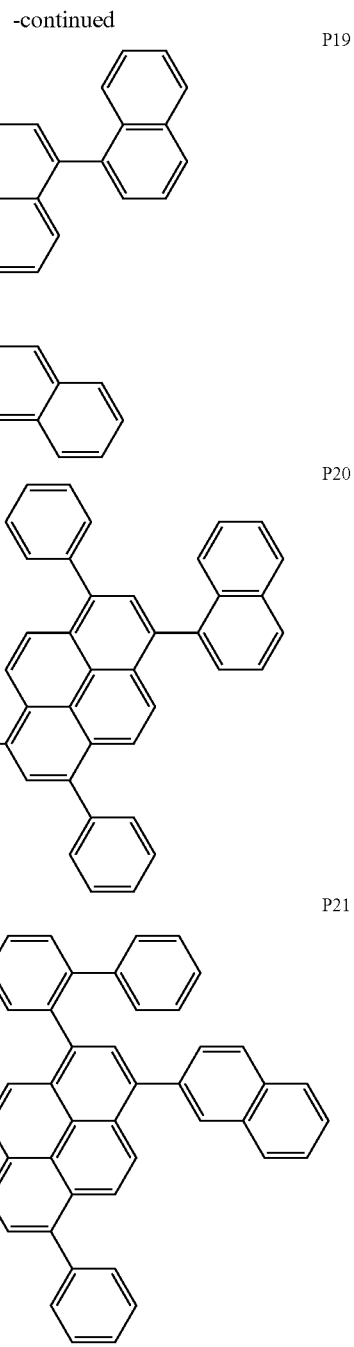

Examples of the organic EL device of a multilayer type include those having multilayer structures such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

The light emitting layer may also optionally contain, in addition to the aromatic amine derivatives of the present invention, conventionally known materials such as light emitting materials, dopants, hole injecting materials and electron injecting materials according to requirements. The organic EL device having such a multilayer structure can be prevented from suffering from deterioration in luminance and lifetime due to quenching. If required, the light emitting materials, dopants, hole injecting materials and electron injecting materials may be used in combination with each other. The use of the dopants enables the resultant device to be improved in luminance and efficiency of light emission, and further emit a red color light or a blue color light. Further, in the organic EL device of the present invention, the hole injecting layer, the light emitting layer and the electron injecting layer may respectively have a multilayer structure including two or more layers. In this case, the multi-layer hole injecting layer may include a hole injecting layer into which holes are injected from the electrode, and a hole transporting layer for accepting the holes from the hole injecting layer and transporting the holes to the light emitting layer. Also, the multilayer electron injecting layer may include an electron injecting layer into which electrons are injected from the electrode, and an electron transporting layer for accepting the electrons from the electron injecting layer and transporting the electrons to the light emitting layer. These respective layers may be selectively used according to various factors such as energy level of the materials used, heat resistance, and adhesion to the organic thin film layers or the metal electrodes.

Examples of the host material or the dopant besides the foregoing general formulae (3) to (5) employable for the light emitting layer together with the aromatic amine derivative of the present invention include fused mass aromatic compound such as naphthalene, phenanthrene, rubrene, anthracene, tetracene, pyrene, perylene, chrysene, decacyclene, coronene, tetraphenylcyclopentadiene, pentaphenyl cyclopentadiene, fluorene, spiro fluorene, 9,10-diphenylanthracene, 9,10-bis(phenyl-ethynyl)anthracene, 1,4-bis(9'-ethynyl anthracenyl)benzene and those derivatives; organometallic complex such as tris(8-quinolinolat)aluminium, bis-(2-methyl-8-quinolinolat)-4-(phenylphenolinat) aluminium, etc.; triarylamine derivative, styryl amine derivative, stilbene derivative, coumarin derivative, pyran derivative, oxazone derivative, benzothiazole derivative, benzoxazole derivative, benzimidazole derivative, pyrazine derivative, cinnamate ester derivative, diketo pyrrolopyrrole derivative, acridone derivative, quinacridon derivative, etc.; though not particularly limited thereto.

The hole injecting material is preferably made of compounds which have a good hole transporting ability as well as excellent capabilities of accepting holes injected from the anode and injecting the holes into the light emitting layer or light emitting material, prevent excited particles produced in the light emitting layer from moving into the electron injecting layer or electron injecting material, and exhibit an excellent capability of forming a thin film. Specific examples of the hole injecting material include phthalocyanine derivatives, naphthalocyanine derivatives, porphyrin derivatives, oxazole, oxadiazole, triazole, imidazole, imidazolone, imidazole thione, pyrazoline, pyrazolone, tetrahydroimidazole, hydrazone, acyl hydrazone, polyaryl alkanes, stilbene, butadiene, benzidine-type triphenyl amine, styryl amine-type triphenyl amine, diamine-type triphenyl amine and derivatives thereof, as well as polyvinyl carbazoles, polysilanes, and high molecular materials such as conductive polymers, though not particularly limited thereto.

Of those hole injecting materials usable in the organic EL device of the present invention, more effective hole injecting materials are aromatic tertiary amine derivatives and phthalocyanine derivatives.

Specific examples of the aromatic tertiary amine derivatives include triphenyl amine, tritolyl amine, tolyldiphenyl amine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cylcohexane, and oligomers and polymers having these aromatic tertiary amine skeletons, though not particularly limited thereto.

Specific examples of the phthalocyanine (Pc) derivatives include phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O—GaPc, as well as naphthalocyanine derivatives, though not particularly limited thereto.

Also, in the organic EL device of the present invention, between the light emitting layer and the anode, there is preferably provided a layer containing these aromatic tertiary amine derivatives and/or phthalocyanine derivatives, such as the above hole transporting layer or hole injecting layer.

The electron injecting material is preferably made of compounds which have a good electron transporting ability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the electron injecting material include fluorenone, anthraquinodimethane, diphenoquinone, thiopyrane dioxide, oxazole, oxadiazole, triazole, imidazole, perylenetetracarboxylic acid, fluorenylidene methane, anthrone, and derivatives thereof, though not particularly limited thereto. Further, an electron accepting substance and an electron donating substance may be added to the hole injecting material and the electron injecting material, respectively, for enhanced sensitization thereof.

In the organic EL device of the present invention, among those electron injecting materials, more effective electron injecting materials are metal complex compounds and nitrogen-containing five-member ring derivatives.

Specific examples of the metal complex compounds include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato) hlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium, though not particularly limited thereto.

The nitrogen-containing five member ring derivatives are preferably derivatives of oxazole, thiazole, oxadiazole, thiadiazole or triazole. Specific examples of the nitrogen-containing five membered ring derivatives include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene, though not particularly limited thereto.

In the organic EL device of the present invention, the light emitting layer may also optionally contain, in addition to the aromatic amine derivatives represented by the general formula (1) or general formula (2), at least one material selected from the group consisting of light emitting materials, dopants, hole injecting materials and electron injecting materials. The organic EL device of the present invention may be further provided on a surface thereof with a protective layer, or the whole part thereof may be protected with silicone oil, resins, etc., in order to enhance stability thereof against temperature, humidity, atmosphere, etc.

The anode of the organic EL device according to the present invention may be suitably made of a conductive material having a work function more than 4 eV. Examples of the conductive material for the anode include carbon, aluminum, vanadium, iron, cobalt, nickel, tungsten, silver, gold, platinum, palladium and alloys thereof, metal oxides such as tin oxide and indium oxide which are used for ITO substrates or NESA substrates, and organic conductive resins such as polythiophene and polypyrrole. The cathode of the organic EL device according to the present invention may be suitably made of a conductive material having a work function of 4 eV or less. Examples of the conductive material for the cathode include magnesium, calcium, tin, lead, titanium, yttrium, lithium, ruthenium, manganese, aluminum, lithium fluoride and alloys thereof, though not particularly limited thereto. Typical examples of the alloys include alloys of magnesium and silver, alloys of magnesium and indium, and alloys of lithium and aluminum, though not particularly limited thereto. The ratio between the constituting metals in the alloys may be controlled and appropriately determined depending upon temperature of vapor deposition sources, atmosphere, vacuum degree, etc. The anode and cathode may be constituted of two or more layers, if required.

At least one surface of the organic EL device of the present invention preferably exhibits a sufficient transparency in a wavelength range of light emitted therefrom in order to enhance an efficiency of light emission thereof. Further, the substrate for the device is also preferably transparent. The transparent electrode is formed using the above conductive material by vapor deposition process, sputtering process, etc., so as to ensure a desirable transparency thereof. The electrode disposed on a light emitting surface of the device preferably has a light transmittance of 10% or more. The substrate is not particularly limited as long as it suitably has a good mechanical and thermal strength as well as a good transparency. Examples of the substrate include glass substrates and transparent resin films. Specific examples of the transparent resin films include films made of polyethylene, ethylene-vinyl acetate copolymer, ethylene-vinyl alcohol copolymer, polypropylene, polystyrene, polymethyl methacrylate, polyvinyl chloride, polyvinyl alcohol, polyvinyl butyral, nylons, polyether ether ketones, polysulfones, polyether sulfones, tetrafluoroethylene-perfluoroalkylvinyl ether copolymer, polyvinyl fluoride, tetrafluoroethylene-ethylene copolymer, tetrafluororethylene-hexafluoropropylene copolymer, polychlorotrifluoroethylene, polyvinylidene fluoride, polyesters, polycarbonates, polyurethanes, polyimides, and polyether imides, polyimide, polypropylene, etc.

The respective layers of the organic EL device of the present invention may be formed by either a dry film-forming process such as vacuum deposition, sputtering, plasma and ion-plating, or a wet film-forming process such as spin-coating, dipping and flow-coating. The thickness of the respective layers is not particularly limited, but should be adjusted to an appropriate range. When the thickness is too large, a large electric voltage must be applied to the device in order to achieve a predetermined light output, resulting in a poor efficiency of light emission. On the other hand, when the thickness is too small, pinholes tend to be formed in the layers, thereby failing to obtain a sufficient luminance of light emitted even upon applying an electric field thereto. The suitable thickness of the respective layers is usually in the range of from 5 nm to 10 μm and preferably from 10 nm to 0.2 μm.

In the wet film-forming process, materials constituting the respective layers are dissolved or dispersed in a suitable solvent such as ethanol, chloroform, tetrahydrofuran and dioxane to form a thin film thereof. The solvent used for forming the respective layers is not particularly limited. Also, suitable resins or additives may be added to the respective organic thin film layers for the purposes of improving a film-forming property, preventing formation of pinholes in the resultant film, etc. Examples of the resins usable for the above purposes include insulating resins such as polystyrene, polycarbonates, polyarylates, polyesters, polyamides, polyurethanes, polysulfones, polymethyl methacrylate, polymethyl acrylate and celluloses as well as copolymers thereof, photoconductive resins such as poly-N-vinyl carbazole and polysilanes, and conductive resins such as polythiophene and polypyrrole. Examples of the additives include antioxidants, ultraviolet absorbers and plasticizers.

The organic EL device of the present invention is suitably applied to, for example, surface light-emitting members such as a wall-type TV flat panel displays, light sources for copiers, printers, back light for liquid crystal displays and, measuring equipments, display panels, marker light, etc. Further, the material of the present invention can be used not only for organic EL devices but also in other applications such as electrophotographic members, photoelectric converters, solar cells, image sensors, etc.

EXAMPLE

The present invention shall be explained below in further details with reference to examples.

Synthesis Example 1

Synthesis of Compound (D-24)

Under an atmospheric argon gas flow, 6,12-dibromochrysene in an amount of 3.8 g (10 mmol), (4'-cyclohexyl phenyl)-3,5-dimethylphenyl amine in an amount of 7.0 g (25 mmol), palladium acetate in an amount of 0.03 g (1.5% by mol), tri-t-butylphosphine in an amount of 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 6.6 g of pale yellow powders were obtained. The pale yellow powders were identified as Compound (D-24) from the result of $^1$H-NMR spectrum (FIG. 1) and Field Desorption Mass Spectrum (FD-MS) measurement (yield: 85%). The $^1$H-NMR spectrum was obtained by means of DRX-500 (Trade name; produced by Brucker Optics Inc.; methylene hydrochloride solvent). Further, the maximum absorption wavelength and the maximum fluorescence wavelength of the obtained Compound (D-24) among the toluene solvent were 407 nm and 453 nm respectively.

Synthesis Example 2

Synthesis of Compound (D-26)

Under an atmospheric argon gas flow, 6,12-dibromochrysene in an amount of 3.8 g (10 mmol), (4'-cyclohexyl phenyl)-

Figure 2:
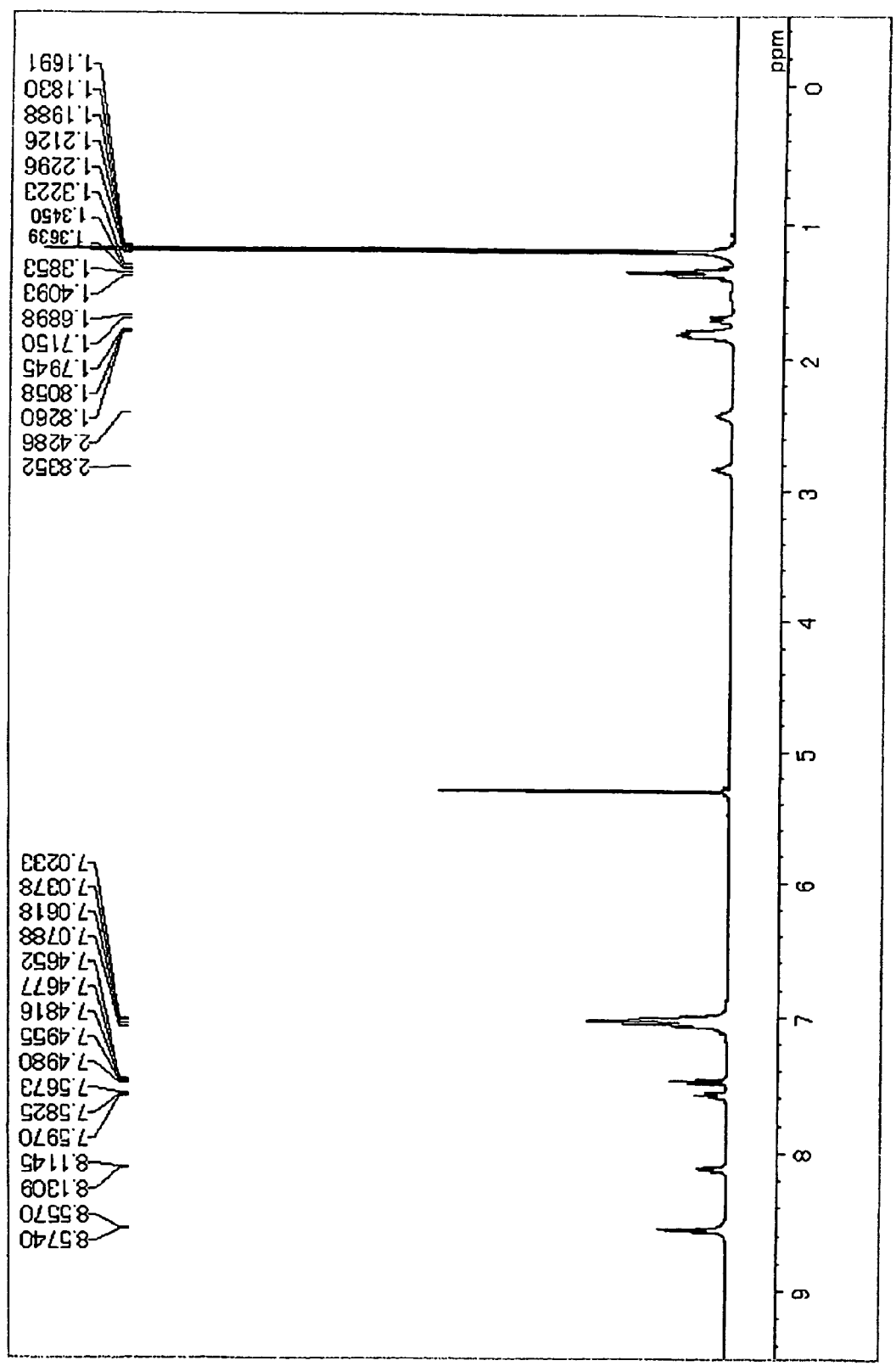
FIG. 2 is a chart showing $^1$H-NMR spectrum of the aromatic amine derivative of the present invention obtained in Synthesis Example 2.

4-isopropylphenyl amine in an amount of 7.3 g (25 mmol), palladium acetate in an amount of 0.03 g (1.5% by mol), tri-t-butylphosphine in an amount of 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 7.7 g of pale yellow powders were obtained. Similarly as Synthesis Example 1, the pale yellow powders were identified as Compound (D-26) from the result of $^1$H-NMR spectrum (FIG. 2) and FD-MS measurement (yield: 95%). Further, the maximum absorption wavelength and the maximum fluorescence wavelength of the obtained Compound (D-26) among the toluene solvent were 407 nm and 455 nm respectively.

Synthesis Example 3

Synthesis of Compound (D-36)

Figure 3:
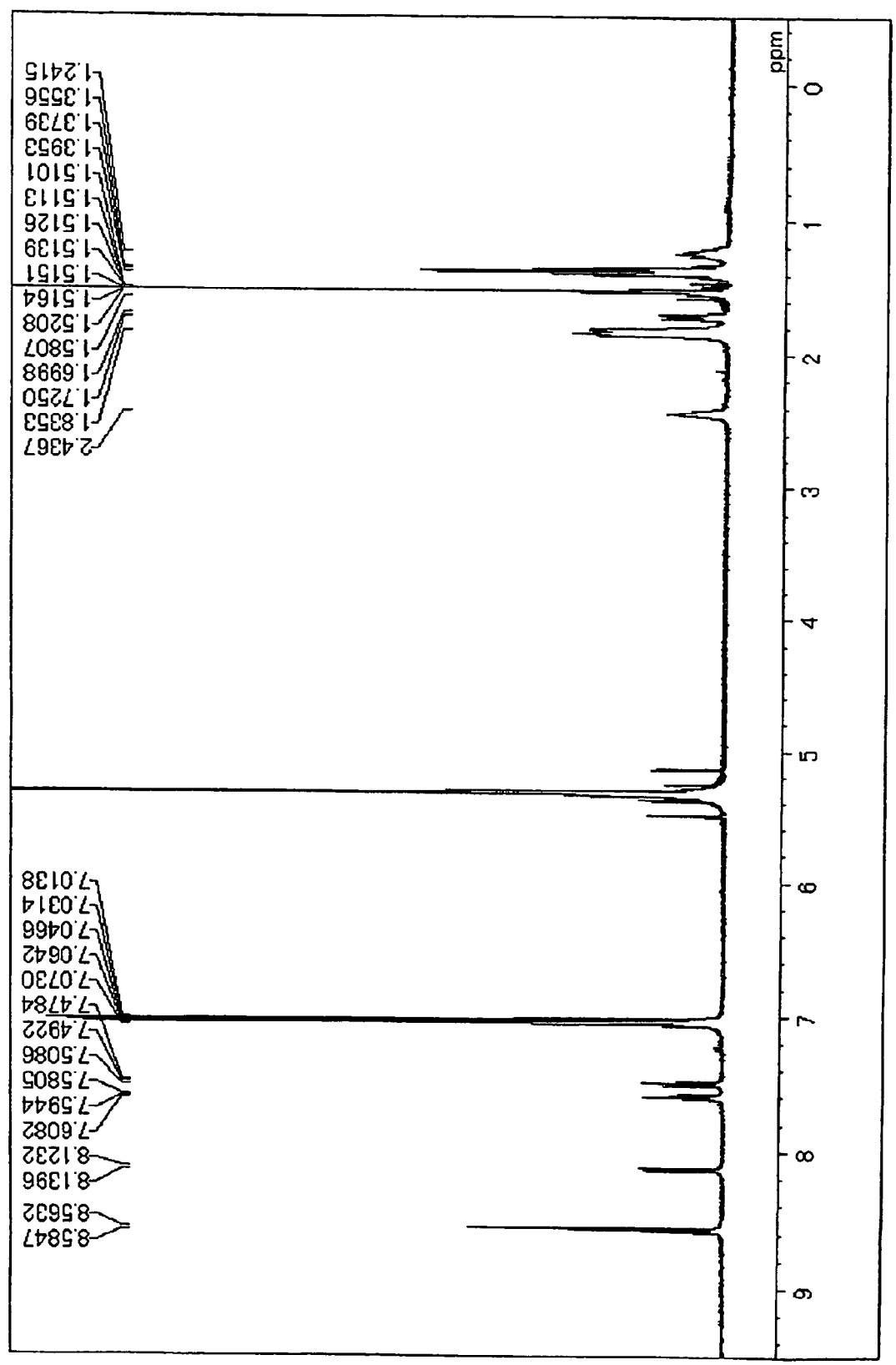
FIG. 3 is a chart showing $^1$H-NMR spectrum of the aromatic amine derivative of the present invention obtained in Synthesis Example 3.

Under an atmospheric argon gas flow, 6,12-dibromochrysene in an amount of 3.8 g (10 mmol), bis(4-cyclohexylphenyl)amine in an amount of 8.3 g (25 mmol), palladium acetate in an amount of 0.03 g (1.5% by mol), tri-t-butylphosphine in an amount of 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 6.7 g of pale yellow powders were obtained. Similarly as Synthesis Example 1, the pale yellow powders were identified as Compound (D-36) from the result of $^1$H-NMR spectrum (FIG. 3) and FD-MS measurement (yield: 78%). Further, the maximum absorption wavelength and the maximum fluorescence wavelength of the obtained Compound (D-36) among the toluene solvent were 409 nm and 457 nm respectively.

Synthesis Example 4

Synthesis of Compound (D-79)

Figure 4:
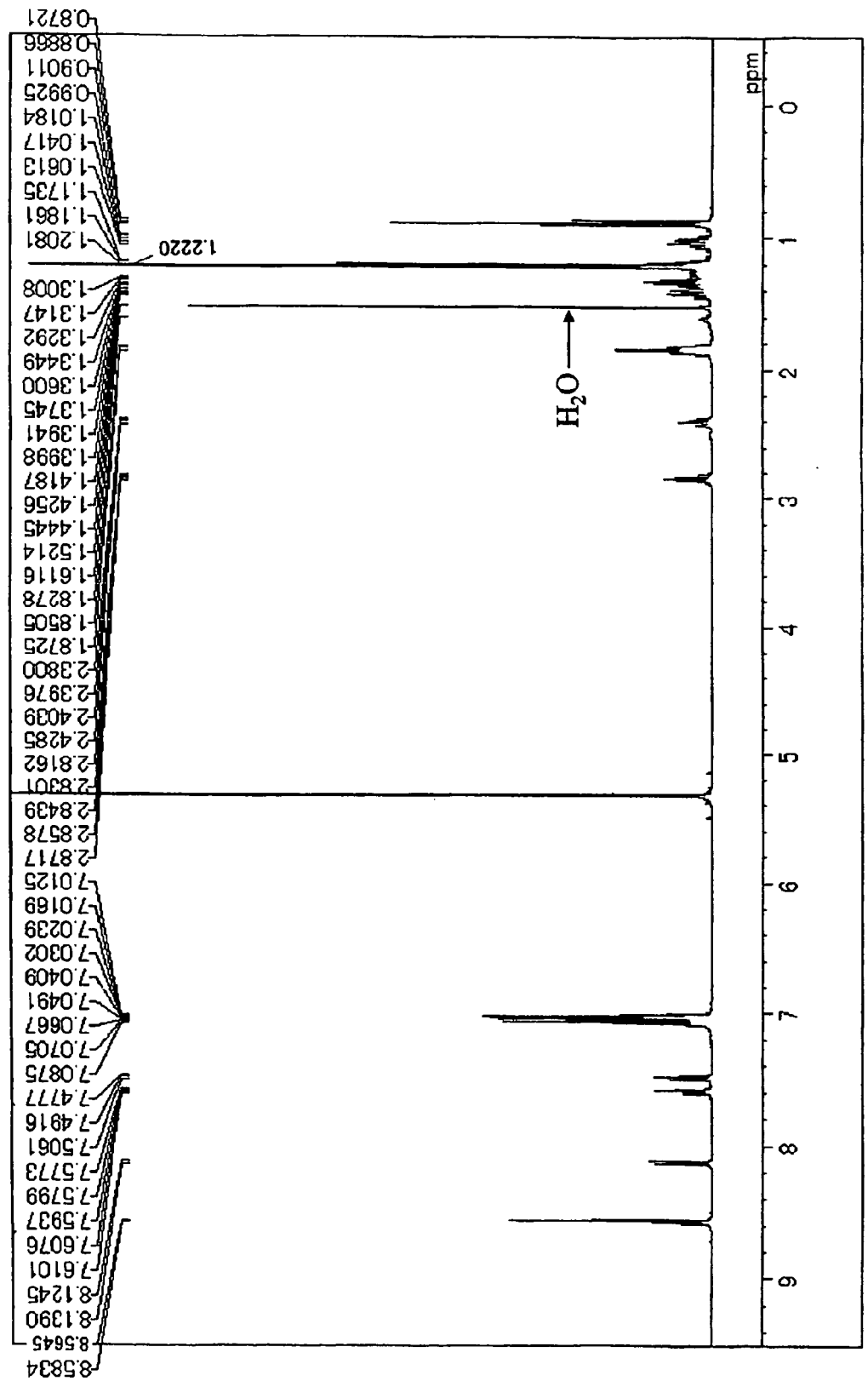
FIG. 4 is a chart showing $^1$H-NMR spectrum of the aromatic amine derivative of the present invention obtained in Synthesis Example 4.

Under an atmospheric argon gas flow, 6,12-dibromochrysene in an amount of 3.8 g (10 mmol), N-(4-isopropylphenyl)-4-(4-propylcyclohexyl) phenylamine in an amount of 8.4 g (25 mmol), palladium acetate in an amount of 0.03 g (1.5% by mol), tri-t-butylphosphine in an amount of 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 8.5 g of pale yellow powders were obtained. Similarly as Synthesis Example 1, the pale yellow powders were identified as Compound (D-79) from the result of $^1$H-NMR spectrum (FIG. 4) and FD-MS measurement (yield: 95%). Further, the maximum absorption wavelength and the maximum fluorescence wavelength of the obtained Compound (D-79) among the toluene solvent were 408 nm and 456 nm respectively.

Example 1

A 120 nm-thick transparent electrode made of indium tin oxide was formed on a glass substrate having a size of 25 mm×75 mm×1.1 mm. The glass substrate with the transparent electrode was cleaned by irradiation of Ultra Violet ray and ozone. The thus cleaned glass substrate with the transparent electrode was mounted to a vacuum vapor deposition apparatus.

First, N',N"-bis[4-(diphenylamino)phenyl]-N',N"-diphenylbiphenyl-4,4'-diamine was vapor-deposited to form a hole injecting layer having a thickness of 60 nm, and then N,N,N',N'-tetrakis(4-biphenyl)-4,4'-bendizine was vapor-deposited on the hole injecting layer to form a hole transporting layer having a thickness of 20 nm. Then, 10,10'-bis[1,1',4',1"]terphenyl-2-yl-9,9'-bianthracenyl and the above Compound (D-26) were simultaneously vapor-deposited at a weight ratio of 40:2 on the hole transporting layer to form a light emitting layer having a thickness of 40 nm.

Next, tris(8-hydroxyquinolinato)aluminum was vapor-deposited on the light emitting layer to form an electron injecting layer having a thickness of 20 nm. Subsequently, lithium fluoride was deposited up to 1 nm in thickness and then, aluminum was deposited up to 150 nm in thickness. The aluminum/lithium fluoride layer works as a cathode. An organic EL device was fabricated in the manner descried above.

As a result of subjecting the obtained organic EL device to a test by feeding electric current, it was confirmed that a blue light with a luminance of 630 cd/m$^2$ (peak wavelength of light emission: 464 nm) and current efficiency of 6.3 cd/A was emitted at a voltage of 6.5 V and a current density of 10 mA/cm$^2$. Further, as a result of subjecting the device to a continuous test by feeding DC electric current starting at an initial luminance of 500 cd/m$^2$, it was confirmed that the half lifetime thereof was 10000 hours.

Example 2

An organic EL device was fabricated in accordance with the same procedures as those conducted in Example 1 except that Compound (D-26) was replaced with Compound (D-22).

As a result of subjecting the obtained organic EL device to a test by feeding electric current, it was confirmed that a blue light with a luminance of 672 cd/m$^2$ (peak wavelength of light emission: 466 nm) and current efficiency of 6.7 cd/A was emitted at a voltage of 6.5 V and a current density of 10 mA/cm$^2$. Further, as a result of subjecting the device to a continuous test by feeding DC electric current starting at an initial luminance of 500 cd/m$^2$, it was confirmed that the half lifetime thereof was 11500 hours.

Example 3

An organic EL device was fabricated in accordance with the same procedures as those conducted in Example 1 except that Compound (D-26) was replaced with Compound (D-24).

As a result of subjecting the obtained organic EL device to a test by feeding electric current, it was confirmed that a blue light with a luminance of 610 cd/m$^2$ (peak wavelength of light emission: 462 nm) and current efficiency of 6.1 cd/A was emitted at a voltage of 6.5 V and a current density of 10 mA/cm$^2$. Further, as a result of subjecting the device to a continuous test by feeding DC electric current starting at an initial luminance of 500 cd/m², it was confirmed that the half lifetime thereof was 8000 hours.

Comparative Example 1

An organic EL device was fabricated in accordance with the same procedures as those conducted in Example 1 except that Compound (D-26) was replaced with 6,12-bis(4-isopropylphenyl-p-tolylamino)chrysene.

As a result of subjecting the obtained organic EL device to a test by feeding electric current, it was confirmed that a blue light with a luminance of 594 cd/m² (peak wavelength of light emission: 462 nm) and current efficiency of 5.9 cd/A was emitted at a voltage of 6.3 V and a current density of 10 mA/cm². Further, as a result of subjecting the device to a continuous test by feeding DC electric current starting at an initial luminance of 500 cd/m², it was confirmed that the half lifetime thereof was 4590 hours.

From the above-mentioned result, it is apparent that when a compound without a cycloalkyl group coupling with an end benzene ring was employed as a material of an organic EL device, half lifetime is shorter than the organic EL devices of Examples 1 to 3 because of an association between compounds each other in Comparative Example 1.

INDUSTRIAL APPLICABILITY

The organic EL device using the aromatic amine derivative according to the present invention exhibits excellent luminance and enhanced efficiency of light emission and further, the device is free from deterioration in properties even after being used for a long period of time and, therefore, has a prolonged lifetime. Resultantly, the EL device is useful as a flat panel light emitting member for a wall-hanging type television or as a light source of backlight and the like for display devices.

What is claimed is:

1. An aromatic amine represented by the following general formula (1):

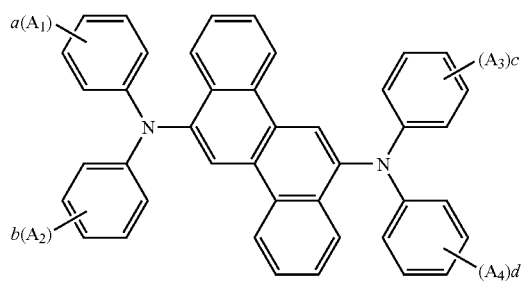

(1)

wherein, $A_1$ to $A_4$ each independently represents a substituted or unsubstituted alkyl group having 1 to 20 carbon atoms, a substituted or unsubstituted aryl group having 5 to 20 ring carbon atoms, or a substituted or unsubstituted cycloalkyl group having 5 to 12 ring carbon atoms a, b, c and d each independently represents an integer of 0 to 5; when a, b, c and d each are 2 or greater, $A_1$ to $A_4$ may be the same with or different from each other, and may bond with each other to form a saturated or unsaturated ring;

wherein at least two of a, b, c and d are integers of 1 or greater, and, at least two of $A_1$ to $A_4$ are substituted or unsubstituted cycloalkyl groups having 5 to 12 ring carbon atoms.

2. The aromatic amine according to claim 1, wherein the at least two of $A_1$ to $A_4$ each independently represents a cyclopentyl group, a cyclohexyl group or a cycloheptyl group.

3. The aromatic amine according to claim 1, wherein $A_1$ to $A_4$ each independently represents methyl group, ethyl group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenylbenzyl group, α,α-ditrifluoromethylbenzyl group, triphenylmethyl group, α-benzyloxybenzyl group, phenyl group, 2-methylphenyl group, 3-methylphenyl group, 4-methylphenyl group, 4-ethylphenyl group, biphenyl group, 4-methyl biphenyl group, 4-ethyl biphenyl group, 4-cyclohexylbiphenyl group, terphenyl group, 3,5-dichlorophenyl group, naphthyl group, 5-methynaphthyl group, anthryl group, pyrenyl group, a cyclopentyl group, a cyclohexyl group or a cycloheptyl group;

the at least two of $A_1$ to $A_4$ each, independently represents a cyclopentyl group, a cyclohexyl group or a cycloheptyl group; and the $A_1$ to $A_4$ may bond each other to form a benzene ring.

4. The aromatic amine according to claim 3, wherein $A_1$ to $A_4$ each independently represents methyl group, ethyl group, propyl group, isopropyl group, butyl group, sec-butyl group, tert-butyl group, benzyl group, phenyl group, 4-methylphenyl group, 4-ethylphenyl group, biphenyl group, naphthyl group, a cyclopentyl group, a cyclohexyl group or a cycloheptyl group.

5. The aromatic amine according to claim 4, wherein $A_1$ and $A_3$ each independently represent methyl group, ethyl, group, propyl group, isopropyl group, butyl group, sec-butyl group, tert-butyl group, benzyl group, phenyl group, 4-methylphenyl group, 4-ethylphenyl group, biphenyl group or naphthyl group, and $A_2$ and $A_4$ each independently represent a cyclopentyl group, a cyclohexyl group or a cycloheptyl group.

6. An aromatic amine represented by the following general formula (2):

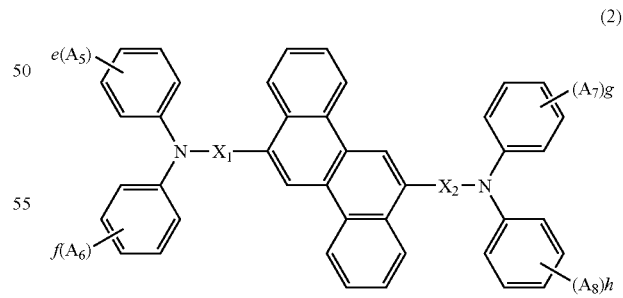

(2)

wherein $A_5$ to $A_8$ each independently represents a substituted or unsubstituted alkyl group having 1 to 20 carbon atoms, a substituted or unsubstituted aryl group having 5 to 20 ring carbon atoms or a substituted or unsubstituted cycloalkyl group having 5 to 12 ring carbon atoms e, f, g and h each independently represents an integer of 0 to 5; when e, f, g and h each are 2 or greater, $A_5$ to $A_8$ may be the same with or different from each other, and may bond with each other to form a saturated or unsaturated ring;

$X_1$ and $X_2$ each independently represents an arylene group selected from the group consisting of phenylene, napthylene, biphenylene, anthranylene, perylenylene and pyrenylene;

wherein, at least two of e, f, g and h are integers of 1 or greater, and in this occasion, at least two of $A_5$ to $A_8$ are a substituted or unsubstituted cycloalkyl group having 5 to 12 ring carbon atoms.

7. The aromatic amine according to claim 6, wherein the at least two of $A_5$ to $A_8$ each independently represents a cyclopentyl group, a cyclohexyl group or a cycloheptyl group.

8. The aromatic amine, according to claim 6, wherein $A_5$ to $A_8$ each independently represents methyl group, ethyl, group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, a-phenoxybenzyl group, α,α-dimethylbenzyl group, α,α-methylphenylbenzyl group, α,α-ditrifluoromethylbenzyl group, triphenylmethyl group, a-benzyloxybenzyl, group, phenyl group, 2-methylphenyl group, 3-methylphenyl group, 4-methylphenyl group) 4-ethylphenyl group, biphenyl group, 4-methyl biphenyl group, 4-ethyl biphenyl group, 4-cyclohexylbiphenyl group, terphenyl group, 3,5-dichlorophenyl group, naphthyl group, 5-methylnaphthyl group, anthryl group, pyrenyl group a cyclopentyl group, a cyclohexyl group or a cycloheptyl group;

the at least two of $A_5$ to $A_8$ each independently represents a cyclopentyl group, a cyclohexyl group or a cycloheptyl group; and the $A_5$ to $A_8$ may bond each other to form a benzene ring.

9. The aromatic amine according to claim 8, wherein $A_5$ to $A_8$ each independently represents methyl group, ethyl group, propyl group, isopropyl group, butyl group, sec-butyl group, tert-butyl group, benzyl group, phenyl group, 4-methylphenyl group, 4-ethylphenyl group, biphenyl group, naphthyl group, a cyclopentyl group, a cyclohexyl group or a cycloheptyl group.

10. The aromatic amine according to claim 9, wherein $A_5$ and $A_7$ each independently represent methyl group, ethyl group, propyl group, isopropyl group, butyl group, sec-butyl group, tert-butyl group, benzyl group, phenyl group, 4-methylphenyl group, 4-ethylphenyl groups biphenyl group or naphthyl group, and $A_6$ and $A_8$ each independently represent a cyclopentyl group, a cyclohexyl group or a cycloheptyl group.

11. The aromatic amine according to claim 1 or 6, which is a dopant for organic electroluminescence device.

12. An organic electroluminescence device which comprises at least one organic thin film layer comprising a light emitting layer sandwiched between a pair of electrodes consisting of an anode and a cathode, wherein at least one of the organic thin film layer comprises the aromatic amine according to claim 1 or claim 6 singly or as its mixture component.

13. The organic electroluminescence device according to claim 12, wherein said light emitting layer comprises the aromatic amine derivative singly or as a mixture of them.

14. The organic electroluminescence device according to claim 12, wherein said light emitting layer comprises the aromatic amine in an amount of 0.1 to 20% by weight.

15. The organic electroluminescence device according to claim 12, which emits bluish light.

* * * * *